United States Patent
Alshaikh et al.

(10) Patent No.: US 11,459,287 B1
(45) Date of Patent: Oct. 4, 2022

(54) ARENE-IMMOBILIZED RU(II)TSDPEN COMPLEXES: SYNTHESIS AND APPLICATIONS TO THE ASYMETRIC TRANSFER HYDROGENATION OF KETONES

(71) Applicant: King Abdulaziz University, Jeddah (SA)

(72) Inventors: Hind Faisal Alshaikh, Jeddah (SA); Julian Knight, Newcastle (GB)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 1 day.

(21) Appl. No.: 17/495,171

(22) Filed: Oct. 6, 2021

(51) Int. Cl.
| | | |
|---|---|---|
| *C07F 15/00* | (2006.01) | |
| *C07C 29/143* | (2006.01) | |
| *B01J 31/18* | (2006.01) | |
| *B01J 31/22* | (2006.01) | |
| *B01J 35/10* | (2006.01) | |
| *B01J 21/08* | (2006.01) | |

(52) U.S. Cl.
CPC ............ *C07C 29/143* (2013.01); *B01J 21/08* (2013.01); *B01J 31/182* (2013.01); *B01J 31/2295* (2013.01); *B01J 35/1057* (2013.01); *B01J 35/1061* (2013.01); *C07F 15/0046* (2013.01); *B01J 2231/643* (2013.01); *B01J 2531/821* (2013.01)

(58) Field of Classification Search
None
See application file for complete search history.

(56) References Cited

U.S. PATENT DOCUMENTS

2013/0158276 A1 * 6/2013 Touge .................. C07C 29/143
549/497

OTHER PUBLICATIONS

Doherty et al. (European Journal of Inorganic Chemistry, 226-235 (Year: 2021).*

* cited by examiner

*Primary Examiner* — Yun Qian
(74) *Attorney, Agent, or Firm* — WCF IP

(57) ABSTRACT

Arene-immobilized Ru(II)TsDPEN Noyori-Ikariya catalysts anchored to silica through the coordinated η6-arene are provided. The catalysts efficiently catalyze many reactions, including the asymmetric transfer hydrogenation of ketones to alcohols.

5 Claims, 3 Drawing Sheets

US 11,459,287 B1

ARENE-IMMOBILIZED RU(II)TSDPEN COMPLEXES: SYNTHESIS AND APPLICATIONS TO THE ASYMETRIC TRANSFER HYDROGENATION OF KETONES

BACKGROUND OF THE INVENTION

Field of the Invention

The invention generally relates to improved reagents and methods of their use to catalyze chemical reactions. In particular, the invention provides arene-immobilized Ru(II) TsDPEN Noyori-Ikariya catalysts anchored to silica through the coordinated η6-arene to catalyze e.g. the asymmetric transfer hydrogenation of ketones to alcohols.

Description of Related Art

The asymmetric hydrogenation of ketones to alcohols is a pivotal transformation in organic synthesis which is widely used in the production of intermediates and pharmaceuticals. [1] The Noyori arene-Ru(II)/TsDPEN system is among the most versatile and efficient catalysts for asymmetric transfer hydrogenation (ATH),[2] using either an azeotropic mixture of formic acid and triethylamine or propan-2-ol as the hydrogen source, as well as asymmetric hydrogenation (AH)[3] and as such numerous modifications have been reported. [4] Although the Noyori-Ikariya catalyst is highly efficient and has been successfully applied in synthetic methodology,[5] the catalyst can be quite costly due to the high catalyst loadings that are often required (0.5-1.0 mol-%) coupled with the expense of the precious metal and a chiral ligand. As such there has been considerable interest in exploring strategies to immobilize this system onto a solid support to facilitate catalyst separation, recovery and reuse as well as improve product purification and enable integration into a continuous flow process for scale up, all of which will ultimately reduce operating costs. One of the most popular approaches to immobilize these systems has been covalent attachment of a nitrogen-modified TsDPEN to an amorphous or mesoporous silica, while retaining the essential key feature of an 'active N—H'.[6]

In recent decades, a number of investigations have been conducted on the development of asymmetric catalysts for hydrogenation reactions because it was found that the correct combination of metal and chiral ligands was crucial for the formation of high-performance catalysts with high catalytic activity and high enantioselectivity in which the hydride donating ability and stereochemical control of the ligands is optimized. [7,8,9]

Enantioselective reduction for various simple ketones is now well established, work that was begun by Noyori and co-workers. The initial study began in 1980, to investigate the use of BINAP functionalized rhodium complexes for enantioselective reduction of α-(acylamino) acrylic acids and esters to produce synthetic amino acids. [10]

More extensive investigations have been explored by Noyori associated with replacing the metal with ruthenium to enhance the activity and extend the substrate scope to include functionalized alkenes containing amides and alcohols.[11] The neighbouring heteroatom on the substrate, for example nitrogen, oxygen or a halide, enables formation of a 4 or 6 membered chelate with the metal and is crucial to attain high enantioselectivity. [11,14]

Noyori subsequently found that using halide ligands instead of carboxylates caused an increase in the performance of the enantioselective catalysts and hence expanded the range of enantioselective reductions to include a variety of ketones. [12,13] For Noyori's first-generation catalyst the mechanism of reduction was proposed to include direct hydrometalation of the carbonyl via a four-membered transition state.

The stereo-determining step in the (R)-BINAP-Ru catalysed hydrogenation using Noyori's first-generation catalyst is the transfer of the hydrogen on Ru transfers to the carbonyl group. For the enantioselective reduction for β-ketoesters, the substrate coordinates to in-plane sites on the metal and the pseudo equatorial phenyl rings on the ligand present a steric blocking arrangement which favours one enantioface of the ketone over the other. The reduction process to form the (S)-enantiomer is disfavoured due to unfavourable non-bonding steric interactions with one of these equatorial phenyl rings in the transition state.[11]

In 1995, ethylenediamine derivatives and potassium hydroxide were discovered to accelerate hydrogenation at the carbonyl group, promoting a change in the reaction mechanism to 6-membered transition state involving the chelated diamine. [14,15] It was found that a ruthenium catalyst constructed of a chiral diamine and chiral diphosphine, such as [RuCl$_2$((S)-xylbinap)((S)-daipen)] as co-catalyst, was highly active and produced high enantioselectivity, e.g. reducing acetophenone using 8 atmosphere of hydrogen gas to obtain 97% conversion and 99% enantiomeric excess in the presence of only 0.001 mol % of catalyst. [16]

The Noyori asymmetric catalyst was further modified by replacing the diamine with a mono-sulfonylated diamine and replacing the diphosphine ligand with an arene. This replacement allowed improved structural variation of the steric properties of the amine as well as the electronic properties of the arene. In addition, the arene forces the catalyst complex into a face-octahedral or 'piano stool' geometry, which constrains the other elements of the catalyst into proximity.[17]

The [(cymene)Ru(TsDPEN)Cl] complex, produced from natural monoterpenes and the commercially available diamine ligand, has formed the basis for the development of the catalyst performance for the asymmetric transfer hydrogenation of ketones. [17,18] Numerous Noyori ATH catalysts have been immobilised onto silica. In 2004 Liu and his group attached a ligand to amorphous and mesoporous silica via the tosyl group of TsDPEN. The supported catalyst was obtained simply by suspending the various silicas in a solution of commercially available [(p-cymene)RuCl$_2$]$_2$. [19] The reduction of acetophenone using immobilised ruthenium complexes occurred in high yield (99% conversion in 6 hours) and enantioselectivity (97% e.e.) using azeotropic formic acid-triethylamine. The reused ruthenium supported on amorphous silica was easily recycled four times by centrifugation to recover the catalyst and then reuse. A 6% reduction of the catalytic activity was observed over 44 hours and also a 30 to 40% reduction in the ruthenium content was observed due to irreversible decomposition, which participated in the decrease in efficiency. On the other hand, compared to the catalyst supported on amorphous silica, the activity of the corresponding catalyst supported on mesoporous silica was substantially poorer. The possible reason for this could be the lack of catalyst surface exposure. [19]

Radical polymerisation of styrene-functionalized silica reactant with a vinyl benzenesulfonyl DPEN analogue was reported to give a silica-immobilised ruthenium complex. This system was characterized by solid-state NMR, and XPS. [20,21] The best recycle results were reported with Noyori catalysts carrying a poly(ethylene glycol) modified TsDPEN. The reduction of acetophenone in aqueous NaO₂CH was reported eleven times without loss of reactivity and/or enantioselectivity, with only 0.4 mol % leaching of Ru. In this PEG-modified system, water reduced the reaction time to only 1 hour. However, the reduction reaction in azeotropic formic acid-triethylamine took more time (about 22 hours) to obtain a 96% yield. The main disadvantage for this reaction system is the somewhat reduced asymmetric induction (93% e.e.). [22]

Arene ruthenium complexes as precatalysts are utilized for many organic reactions, for example olefin cyclopropanation, olefin metathesis and transfer hydrogenation. The significant drawbacks of using these complexes are that they are often moisture- and air-sensitive, expensive and cannot be reused. For that reason, the development of arene complexes has focused on solving these problems. Several studies found that stabilization occurred by immobilising the arene ruthenium complexes into a polymer. [(arene)Ru(TsDPEN)Cl] catalyst was used to immobilise the Ru complex onto polymer via the arene ligand in 2005 by the Wendicke group. A bridged pre-catalyst was prepared by condensing 2-hydroxyethyl methacrylate with 2-methylcyclohexa-2,5-diene-1-carboxylic acid followed by reacting with ruthenium trichloride. Radical polymerization of the ruthenium dimer with the cross-linking monomer EGDMA was followed by active catalyst formation in-situ by adding TsDPEN. [23]

In contrast to the myriad of examples of solid-supported Noyori-Ikariya-type catalysts immobilized through the TsDPEN ligand, there appears to be only a single report of immobilization through the π-arene ring.[24] This system was prepared by polymerization of methacrylate side chain-modified [(arene)RuCl₂]₂ with ethyleneglycol dimethacrylate and the resulting polymers combined with TsDPEN to form an efficient catalyst for the ATH of ketones.

There are no reports of silica-supported precatalysts tethered via the η6-coordinated arene, which is somewhat surprising considering there are numerous advantages associated with the use an ordered mesoporous silica as a support for anchoring chiral transition metal catalysts; these include control of surface area and pore volume, tunable pore dimensions, potential for functionalization and good thermal and mechanical integrity.[25]

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

This disclosure provides the first examples of (arene)Ru(TT)/TsDPEN-based Noyori-Ikariya precatalysts anchored to silica through the coordinated η6-arene and their application to the asymmetric transfer hydrogenation of ketones and other reactions.

It is an object of this invention to provide an arene-Ru (II) catalyst having the formula

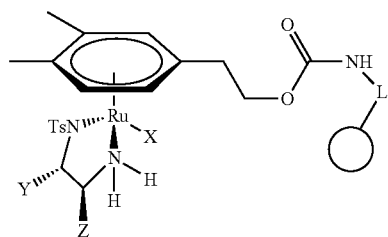

wherein X is a halogen or CN,
Y and Z are the same or different and each is a carbon ring structure;
L is a carbon-based linker; and
○ is a silica support.

In some aspects, the arene-Ru (II) catalyst has the formula:

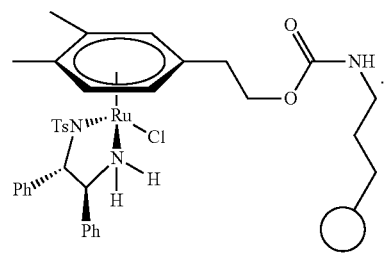

In some aspects, the silica support is silica gel, a silica composite, amorphous silica, COK-12 silica, or MCM-41 silica. In further aspects, the silica support is silicon dioxide particles having a pore size of 30 Å.

Also provided is a method of catalyzing asymmetric hydrogenation of a ketone, comprising contacting the ketone with a hydrogen donor in the presence of the arene-Ru (II) catalyst having the formula

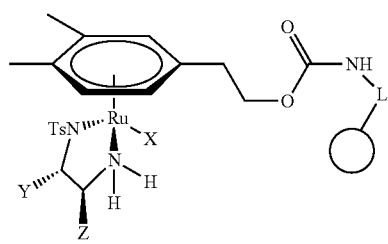

wherein X is a halogen or CN,
Y and Z are the same or different and each is a carbon ring structure;
L is a carbon-based linker; and
○ is a silica support.

In some aspects, the ketone is:

-continued

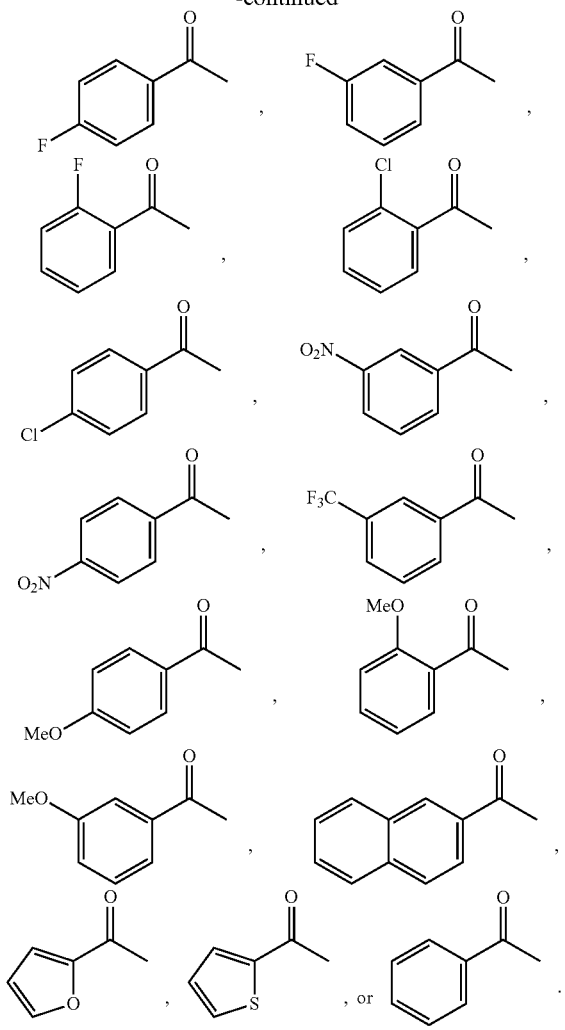

In additional aspects, the hydrogen donor is $HCO_2H/NEt_3$, $Me_2NHBH_3$, $NaBH_4$, $KO_2CH$, $NH_4O_2CH$ or $HCO_2H$. In yet further aspects, the method is conducted by or incorporated into a continuous flow process. In some aspects, the arene-Ru (II) catalyst is generated in situ.

Also provided is a method of catalyzing conversion of a ketone to an alcohol comprising, contacting the ketone with the arene-immobilized Ru(II)TsDPEN Noyori-Ikariya catalyst having the formula

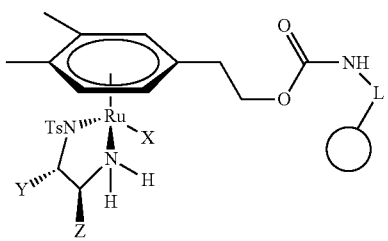

wherein X is a halogen or CN; Y and Z are the same or different and each is a carbon ring structure; L is a carbon-based linker; and ○ is a silica support; wherein the step of contacting is performed in the presence of a hydrogen donor, and wherein the step of contacting is performed under conditions that permit asymmetric transfer hydrogenation conversion of the ketone to form the alcohol.

DETAILED DESCRIPTION

Figure 1:
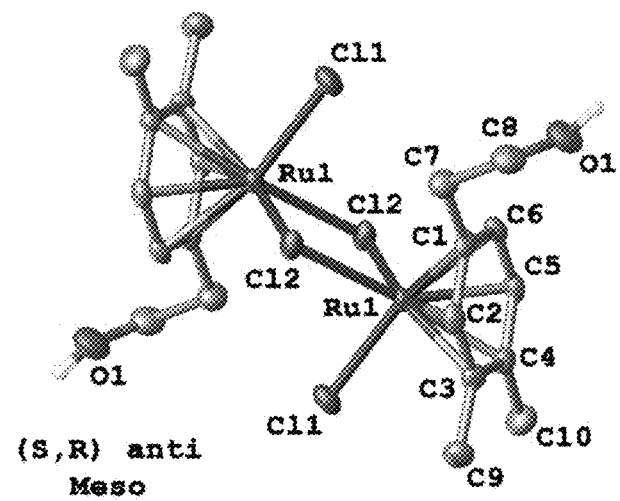
FIG. 1. Crystal structure of [(2-(3,4-dimethylphenyl) ethan-1-ol)RuCl$_2$]$_2$ (4). Hydrogen atoms have been omitted for clarity except those of the hydroxyl groups. Ellipsoids are drawn at the 50% probability level.

This disclosure provides Noyori-Ikariya (arene)Ru(II)/ TsDPEN catalysts anchored to amorphous silica and DAVI-SIL® through the η6-coordinated arene ligand. Exemplary catalysts, e.g. (arene)Ru(II)/TsDPEN@silica and (arene)Ru (II)/TsDPEN@DAVISIL®, are highly efficient catalysts for, for example, the asymmetric transfer hydrogenation of a range of electron-rich and electron-poor aromatic ketones, giving good conversion and excellent ee's under mild reaction conditions. Moreover, catalysts generated in situ immediately prior to addition of substrate and hydrogen donor, by reaction of silica-supported [(arene)RuCl$_2$]$_2$ with (S,S)-TsDPEN, were as efficient as those generated from a preformed counterpart e.g. [(arene)Ru{(S,S)-TsDPEN}Cl] @silica. The initial TOFs (up to 1085 h$^{-1}$) and ee's (96-97%) obtained with these catalysts either rivalled or outperformed those previously reported for catalysts supported by either silica or polymer immobilized through one of the nitrogen atoms of TsDPEN. High ee's were also maintained during recycle studies.

Definitions

As used herein a precatalyst (plural precatalysts) is a compound that is converted to a catalyst. Conversion may be prior to use for catalyzing a chemical reaction or in situ, as a step of the entire reaction process.

"Ee" refers to "enantiomeric excess". Kinetic resolution is a means of differentiating two enantiomers in a racemic mixture and relies on the different chemical properties of racemic starting materials. In kinetic resolution, two enantiomers react with different reaction rates in a chemical reaction with a chiral catalyst or reagent, resulting in an enantioenriched sample of the less reactive enantiomer. The enantiomeric excess (ee) of unreacted starting material continually rises as more product is formed, reaching 100% just before full completion of the reaction.

1,2-Diphenyl-1,2-ethylenediamine, DPEN, is an organic compound with the formula $H_2NCHPhCHPhNH_2$, where Ph is phenyl ($C_6H_5$). DPEN exists as three stereoisomers: meso and two enantiomers S,S- and R,R-. The N-tosylated derivative, TsDPEN, is a ligand precursor for catalysts for asymmetric transfer hydrogenation.

The Catalysts

The catalysts described herein comprise (arene)Ru(II)/TsDPEN. In the catalysts, the active catalytic group is ultimately anchored to a support through the η6-coordinated arene ligand. The step of anchoring (attachment, immobilization, tethering, etc.) may be performed before the catalyst is used to catalyze a reaction or may be performed in situ, i.e. the catalysts components combined and permitted to react (without substrates being present) and then the catalyst is combined with reactants. If the reactions are conducted in a continuous flow system, the catalyst may be formed e.g. in a reaction chamber which is then drained and washed, and then the reactants are added and the reaction ensues to form the desired product(s). Each step of reacting is performed in a suitable medium.

In some aspects, the catalysts have the formula shown as Formula I below:

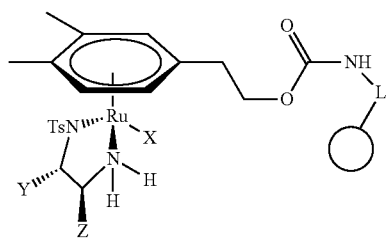

Formula I where: X is halogen, examples of which include but are not limited to: Cl, F, Br, I, etc., or X is CN; (for example, if X is first Cl, Cl can be replaced by CN as described in Vinoth et al. Elsevier Inorganica Chimica ActaVolume 514, 1 Jan. 2021, 120006, the complete contents of which is hereby incorporated by referenced in entirety);

Y and Z are the same or different and each is a carbon ring structure;

L is a carbon-based linker; and

○ is a silica support.

Y and Z are the same or different and each is a monocyclic or multicyclic carbon ring structure (e.g. di- or tri-cyclic). Each carbon ring generally comprises from about 5 to about 8 carbon atoms and may be saturated or unsaturated. If unsaturated, each carbon ring can comprise from about 1 to about 3 double bonds. In some aspects, the carbon rings are aryl. In some aspects, a carbon ring is unsubstituted. In some aspects, a carbon ring is substituted (a carbon atom within the ring is replaced by a heteroatom). If substituted (i.e. the ring is a heterocycle), the heteroatoms include, for example, N, O, S. In some aspects, various functional groups are attached to a carbon or heteroatom of the ring, e.g. COOH, sulfate, nitrate, alkyl groups, halogen, etc.

In some aspects, a carbon ring is: phenyl; substituted phenyl (e.g. mono- or di-substituted phenyl); a C1-6 aliphatic and/or 3- to 8-membered carbocyclyl group; a 5-6 membered heteroaryl group containing e.g. 1-3 heteroatoms; optionally substituted pyridyl; wherein when these groups are "optionally substituted", a carbon atom is substituted by a heteroatom that is independently selected from nitrogen, oxygen, and sulfur;

L is a linker (a carbon-based or carbon containing linker) that connects (links, tethers, immobilizes, attaches, connects, etc.) a support to the benzyl ring of the catalyst via the N atom of COONH, examples of which include but are not limited to: unbranched or branched, saturated or unsaturated carbon groups or chains comprising e.g. about 1-10 carbon atoms, i.e. about 1, 2, 3, 4, 5, 6, 7, 8, 9, or 10 carbon atoms. In some aspects, the linker is a straight saturated alkyl chain having about 1-10 carbon atoms, such as methyl, ethyl propyl, butyl, pentyl, hexyl, heptyl, octyl, nonyl, decyl, etc. In other aspects, the saturated alkyl chain is branched. In other aspects, the linker is an unsaturated carbon chain having e.g. about 1-3 double bonds. Examples of carbon chains with one double bond (i.e. an alkene) include but are not limited to: ethylene, propylene, 1-butene, 2-butene, isobutylene, 1-pentene, 2-pentene, 2-methyl-1-butene, 3-methyl-1-butene, 2-methyl-2-butene, 1-hexene, 2-hexene, 3-hexene, methylpentene, dimethylbutane, etc.

○ is a support. In some aspects, the support is a porous or non-porous silica support, examples of which include but are not limited to: amorphous silica, silica gel, a silica composite, colloidal silica, a mixed oxide such as silica-alumina, various functionalized ordered mesoporous silicas such as [MCM-41], [COK-12] [KIT-6], and [SBA-15]; various so-called DAVISIL® silica supports such those having distinct pore diameters e.g. of about 30 Å (such as DAVISIL® grade 923 comprising silicon dioxide made from sodium silicate having a pore size of about 30 Å and a mesh of from 100 to 200). It is a granular and porous solid which are readily commercially available at e.g. Grace, Thomas Scientific, etc. In some aspects, the catalytic component of the catalyst is supported on and/or in a silica (SiO$_2$) catalyst support wherein the average pore diameter of the catalyst support is more than 10 nm but less than 100 nm, such as about 10, 20, 30, 40, 50, 60, 70, 80, 90 or 100 nm, or a mixture of these pore sizes.

Additional silica support compositions are described, for example, in issued U.S. Pat. No. 4,617,060A, the complete contents of which is hereby incorporated by reference in entirety.

In some aspects, the catalyst has the following formula:

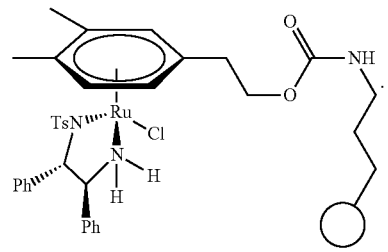

Reactions that are Catalyzed

Numerous chemical reactions can be catalyzed using the catalysts described herein. Examples of such reactions include but are not limited to: the asymmetric transfer hydrogenation of ketones (especially a range of electron-rich and electron-poor aromatic ketones) to form alcohols; 1,4-additions to conjugated enones, hydrosilylations, arene hydrogenation, oxidation of alcohols, Diels-Alder cycloadditions, cyclopropanation, the hydrocarboxylation of alkynes, ring-opening and ring-closing metathesis, etc. The present catalysts catalyze one or more steps of such reactions.

With respect to the asymmetric transfer hydrogenation of ketones, a "ketone" includes a carbonyl functional group (a carbon-oxygen double bond) and has the structure R2C=O, where R can be a variety of carbon-containing substituents and the two R constituents may be the same (R and R) or different (e.g. R and R'). Exemplary R or R and R' groups include but are not limited to: saturated or unsaturated, straight or branched and unsubstituted carbon chains and carbon chains substituted with one or more heteroatoms replacing carbon in a chain; saturated or unsaturated and unsubstituted carbon mono-, di- or tri-cyclic groups having e.g. about 3-8 carbons and optionally substituted with one or more heteroatoms replacing carbon in within at least one ring (i.e. heterocycles); various aryl groups which are optionally substituted with one or more heteroatoms replacing carbon in within the ring; etc. Heteroatoms include but are not limited to: O, N, S. Non-carbon atoms or functional groups may also be attached to the cyclic and aryl rings, including but not limited to, for example, halogen atoms, sulfate, nitrate, carbonyl.

Examples of ketones that can be converted to alcohols by the catalysts disclosed herein include but are not limited to:

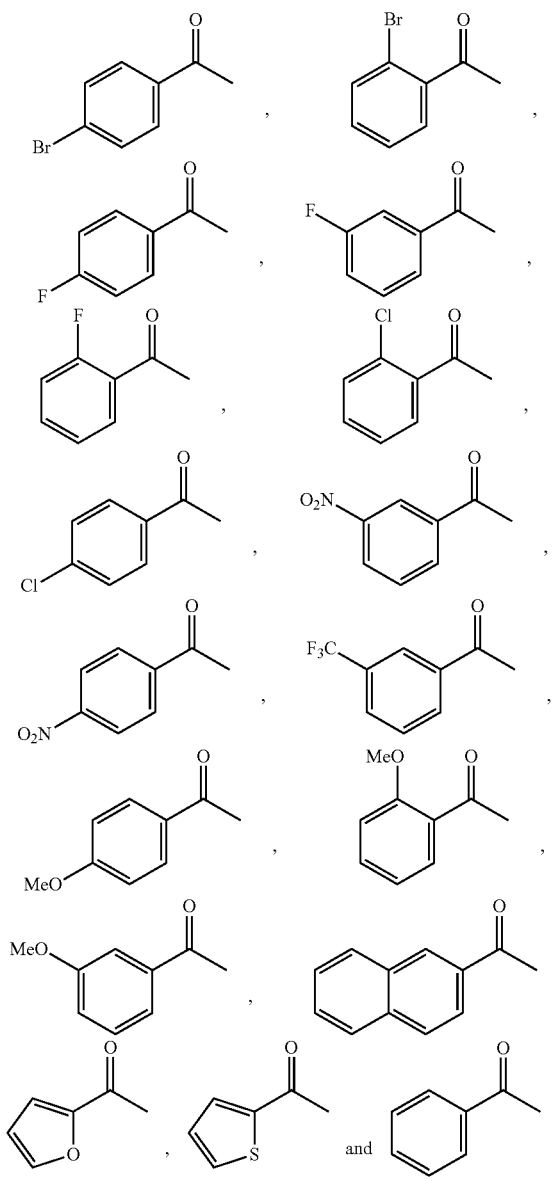

The reactions that are catalyzed as described herein are carried out in the presence of at least one hydrogen donor (reducing agent). Examples of suitable H-donors that are used include but are not limited to: $H_2$ gas, $HCO_2H/NEt_3$, $Me_2NHBH_3$, $NaBH_4$, $KO_2CH$, $NH_4O_2CH$, $HCO_2H$, etc.

Media for carrying out the reactions disclosed here can be any which are suitable to solubilize reactants and not interfere with the reaction. Examples include but are not limited to: water; alcohol (e.g. ETOH, MeOH, etc.); formic acid; triethylamine; etc. and combinations of these. For example, an azeotrope (a mixture of two liquids which has a constant boiling point and composition throughout distillation) such as a formic acid-triethylamine azeotrope may be used.

The reactions are carried out at any of a variety of temperatures that are compatible with good yields. Generally, the temperature ranges from about 15 to about 60° C., such as about 15, 20, 25, 30, 35, 40, 45, 50, 55 or 60° C.

The reaction times are any which are necessary to give the desired yield of product and range from a few minutes (e.g. about 1-10 minutes) or longer such as about 30, 45 or 60 minutes or longer, if warranted.

In some aspects, the catalysts are integrated into a continuous flow process for scale-up. As is known in the art, flow chemistry (continuous processing, continuous flow chemistry) begins with two or more streams of different reactants pumped at specific flow rates into a single chamber, tube, or microreactor. A reaction takes place, and the stream containing the product is collected at an outlet. In some aspects, the product(s) is/are intermediates and is/are further reacted in second, third, etc. reaction chambers until a final desired product is produced.

In further aspects, the catalysts are multifunctional catalysts for cascade reaction sequences. Examples include but are not limited to the syntheses of: N-4-tert-butylbenzene-sulfonyl-4,5-dichloro-o-phenylenediamine, N-benzene-sulfonyl-4,5-dichloro-o-phenylenediamine, and N-4-methoxybenzenesulfonyl-4,5-dichloro-o-phenylenediamine, etc.

In one aspect, the catalysts, e.g. in cascade reaction sequences, are used for the conversion of biomass derived substrates into value-added products. Examples include but are not limited to reactions that form 2,5-diformylfuran, 2,5-furandicarboxylic acid, 5-formyl-2-furancarboxylic acid, maleic anhydride, 2,5-furandimethylcarboxylate, 5-hydroxy-5-(hydroxymethyl)furan-2(5H)-one, 2,5-dimethylfuran, 2,5-dimethyltetrahydrofuran, 2,5-dihydroxymethyl-tetrahydrofuran, 1-hydroxyhexane-2,5-dione, 1,2,6-hexanetriol, 5,5-bis(hydroxymethyl)furoin, 5-arylaminomethyl-2-furanmethanol, 5-alkanoyloxymethyl-furfural, and 5,5-oxybis(methylene-2-furaldehyde), etc.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

¥

Example

The asymmetric hydrogenation of ketones to alcohols is a pivotal transformation in organic synthesis which is widely used in the production of intermediates and pharmaceuticals. [1] The Noyori arene-Ru(II)/TsDPEN system is among the most versatile an efficient catalysts for asymmetric transfer hydrogenation (ATH),[2] using either an azeotropic mixture of formic acid and triethylamine or propan-2-ol as the hydrogen source, as well as asymmetric hydrogenation (AH)[3] and as such numerous modifications have been reported. [4] Although the Noyori-Ikariya catalyst is highly efficient and has been successfully applied in synthetic methodology,[5] the catalyst can be quite costly due to the high catalyst loadings that are often required (0.5-1.0 mol-%) coupled with the expense of the precious metal and a chiral ligand. As such there has been considerable interest in exploring strategies to immobilize this system onto a solid support to facilitate catalyst separation, recovery and reuse as well as improve product purification and enable integration into a continuous flow process for scale up, all of which will ultimately reduce operating costs.

One of the most popular approaches to immobilize these systems has been covalent attachment of a nitrogen-modified TsDPEN to an amorphous or mesoporous silica, while retaining the essential key feature of an 'active N—H'.[6] In addition, while TsDPEN grafted by covalent attachment of nitrogen to polystyrene[7] and PEG[8] have both been used to immobilize these catalysts with varying levels of success, Xiao developed an alternative approach to immobilizing TsDPEN by attachment to poly(ethylene glycol) via both of its phenyl rings; the corresponding Noyori-Ikariya catalyst is among the most efficient to be reported with fast reaction rates, excellent ee's and outstanding reusability.[9] Other methods used to immobilize (arene)Ru(II)/TsDPEN and facilitate its recovery and reuse include modification of TsDPEN with an imidazolium[10] or phosphonium[11] group for use in ionic liquids and water, respectively, and incorporation of the diamine into a Fréchet-type core-functionalized dendrimer.[12] In more recent developments, (arene)Ru(II)/TsDPEN has been anchored to a support which also incorporates a palladium-based catalyst for cross-coupling and the resulting switchable bifunctional system used as a catalyst for enantioselective cascade reaction sequences.[13]

In contrast to the myriad of examples of solid-supported Noyori-Ikariya-type catalysts immobilized through the TsDPEN ligand, there appears to be only a single report of immobilization through the η-arene ring.[14] This system was prepared by polymerization of methacrylate side chain-modified [(arene)RuCl$_2$]$_2$ with ethyleneglycol dimethacrylate and the resulting polymers combined with TsDPEN to form an efficient catalyst for the ATH of ketones. However, to the best of our knowledge there are no reports of silica-supported precatalysts tethered via the η6-coordinated arene. There are numerous advantages associated with the use of an ordered mesoporous silica as a support for anchoring chiral transition metal catalysts; these include control of surface area and pore volume, tunable pore dimensions, potential for functionalization and good thermal and mechanical integrity.[15] Thus, our interest in developing such an arene-anchored catalyst is four-fold, firstly, the straightforward and versatile synthesis of a range of functionalized 1,4-cyclohexadienes via cycloaddition would lend itself to catalyst modification and diversification, secondly, a library of catalysts could be generated either before or after silanization by introduction of a suitable chiral diamine or amino alcohol, thirdly, anchoring the catalyst to the support via the arene ring avoids modification of the basic nitrogen atom of Ts-DPEN which has been reported to reduce catalyst activity and enantioselectivity and, finally, arene ruthenium complexes have also been used in a host of other transformations including; 1,4-additions to conjugated enones,[16] hydrosilylations, [17] arene hydrogenation, [18] oxidation of alcohols, [19] Diels-Alder cycloadditions, [20] cyclopropanation, [21] the hydrocarboxylation of alkynes [22] and ring-opening and ring-closing metathesis [23] and as such this strategy has much broader applications.

Herein we report the first examples of an (arene)Ru(II)/TsDPEN-based Noyori-Ikariya precatalyst anchored to silica through the coordinated η6-arene and its application to the asymmetric transfer hydrogenation of ketones. The conversions and ee's obtained with these catalysts either rivalled or outperformed those obtained with their homogeneous counterparts as well as systems immobilized on either silica, a polymer or PEG through one of the nitrogen atoms of the TsDPEN.

Results and Discussion
Synthesis of Silica-Supported (Arene)Ru(II) Dimers (6 and 7), the Corresponding Precatalysts (8 and 9) and Molecular Precatalyst (10).

The key to immobilizing the (arene)Ru(II) fragment via the arene ligand is access to an appropriately substituted 1,4-cyclohexadiene which can be further modified to introduce a silanizable triethoxysilyl group after coordination to ruthenium (Scheme 1). This was achieved via the cobalt catalyzed cycloaddition between 2,3-dimethyl-1,3-butadiene 1 and 3-but-1-ynol 2 to afford the 1,4-cyclohexadiene 3 as a clear spectroscopically pure oil after purification by distillation (Scheme 1).[24] The corresponding (arene)ruthenium(II) dimer 4 was prepared by reaction of 3 with ruthenium trichloride in 2-methoxyethanol and isolated as a pale orange solid in near quantitative yield by precipitation with diethyl ether. As each ruthenium fragment has a stereogenic plane, 4 could exist as a mixture of rac and meso diastereoisomers. Interestingly though, the 1H NMR and $^{13}C\{^1H\}$ NMR spectra appear to contain only one set of resonances with no evidence for a second diastereoisomer; this may be due to either (i) formation of a single diastereoisomer, (ii) rapid interconversion of a mixture of diastereoisomers via facile dissociation of the kinetically labile chloride bridges or (iii) formation of a mixture of diastereoisomers that are indistinguishable by NMR spectroscopy. Crystallisation of 4 by slow evaporation of a concentrated ethanol solution at room temperature gave crystals suitable for a single-crystal X-ray study; a perspective view of the molecular structure is shown in FIG. 1. The molecular structure shows that the crystal used to collect the data contains the (S,R) anti-diastereoisomer although this does not conclusively prove that 4 exists as a single diastereoisomer in solution. The Ru—C(arene) bond lengths fall between 2.149(3) and 2.200(3) Å with a mean value of ca. 2.18 Å, which is within the range reported for related complexes such as [(p-cymene)RuCl$_2$]$_2$ (range: 2.13(1)-2.18(2) Å; mean: ca. 2.16 Å),[25] [(C$_6$H$_5$OCH$_2$CH$_2$OH)RuCl$_2$]$_2$ (range: 2.14(1)-2.21(1) Å; mean: ca. 2.17 Å),[26] [1,4-C6H$_4$(CH$_2$CO$_2$Et)2)RuCl$_2$]$_2$ (range: 2.150(5)-2.182(5) Å; mean: ca. 2.17 Å)[27] and [(C$_6$H5CH$_2$CO$_2$H)RuCl$_2$]$_2$ (range: 2.15(1)-2.184(8) Å; mean: ca. 2.16 Å).[28] The Ru—Cl bond lengths of 2.4152(8) Å (monodentate) and ca. 2.44 Å (bridging) are also unexceptional and similar to the mean value for those observed in this series of (arene)Ru-dimers (ca. 2.40 Å (monodentate) and ca. 2.45 Å (bridging).

Figures 2A, 2B:
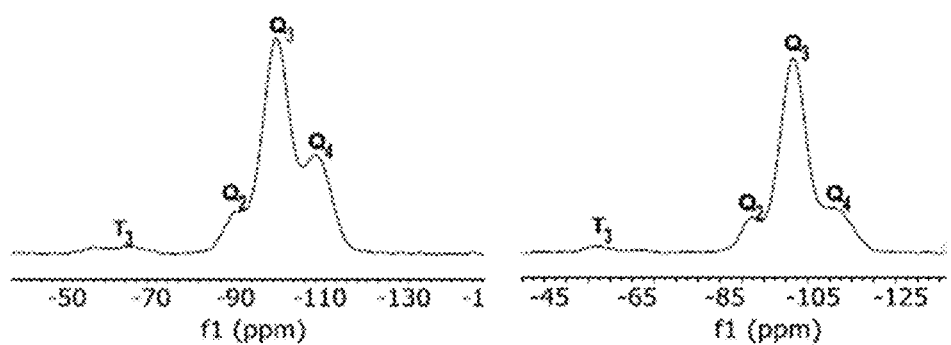
FIGS. 2A and B. Solid state $^{29}Si$ CP MAS NMR spectra of (a) 7 and (b) precatalyst 9.

The silanizable triethoxysilane-containing extension was introduced by reaction of the alcohol 4 with triethoxy(3-isocyanatopropyl)silane to afford the corresponding carbamate 5 in 80% yield after washing the crude product with dry hexane to remove excess isocyanate. The identity of 5 was established by $^1$H NMR spectroscopy, IR spectroscopy and the electrospray mass spectrum which contained an ion with an m/z at 534.1011 corresponding to the [Ru(arene)Cl]$^+$ fragment. (Arene)Ru(II) dimer 5 is a highly versatile fragment that can be immobilised on a range of silica supports and subsequently reacted with a chiral ligand to generate a library of catalysts. Amorphous silica and DAVISIL® were identified as suitable supports; this was achieved by heating 5 and the silica in a range of solvents at reflux. Reaction times were varied and the extent of silanization determined as a function of time by filtering the reaction mixture to remove the silica and then analysing the remaining solution by $^1$H NMR spectroscopy, using 4-bromobenzonitrile as an internal standard to quantify the amount of 5 that had not been immobilised. The most efficient silanization was achieved in toluene after 24 h. In addition, as the 11-arene ligand is known to undergo exchange at elevated temperatures, the stability of 5 in toluene was monitored at 120° C. for 24 h; under these conditions there was no evidence for dissociation of the arene in 5. Under these conditions, 5 was immobilized on amorphous silica and DAVISIL® to afford 6 and 7, respectively, in near quantitative yields. DAVISIL® was chosen as it is a high surface area amorphous silica (pore size 6 nm, 450-560 m$^2$ g$^{-1}$) and as such the active sites are expected to be exposed and accessible on the surface of the support, whereas for mesoporous materials with a hierarchical structure such as MCM-41 and SBA-15 the active sites are more likely to be encapsulated in pores; moreover a wide range of pore diameters is commercially available which will ultimately enable the influence of the pore size on catalyst efficacy to be explored in a systematic manner. The amorphous silica used for comparison has a slightly smaller pore size of 4 nm and a correspondingly higher BET surface area of >700 m$^2$ g$^{-1}$. The ruthenium loadings of 6 and 7 were determined to be 0.023 and 0.037 mmol g-1, respectively, by ICP-OES which corresponds to a loading of 0.23 and 0.37 wt-%, respectively, and the solid state $^{13}$C and $^{29}$Si cross-polarization magic angle spinning NMR spectra confirmed that the ruthenium dimer was immobilized onto the silica walls of an inorganosilicate network (FIG. 2a).

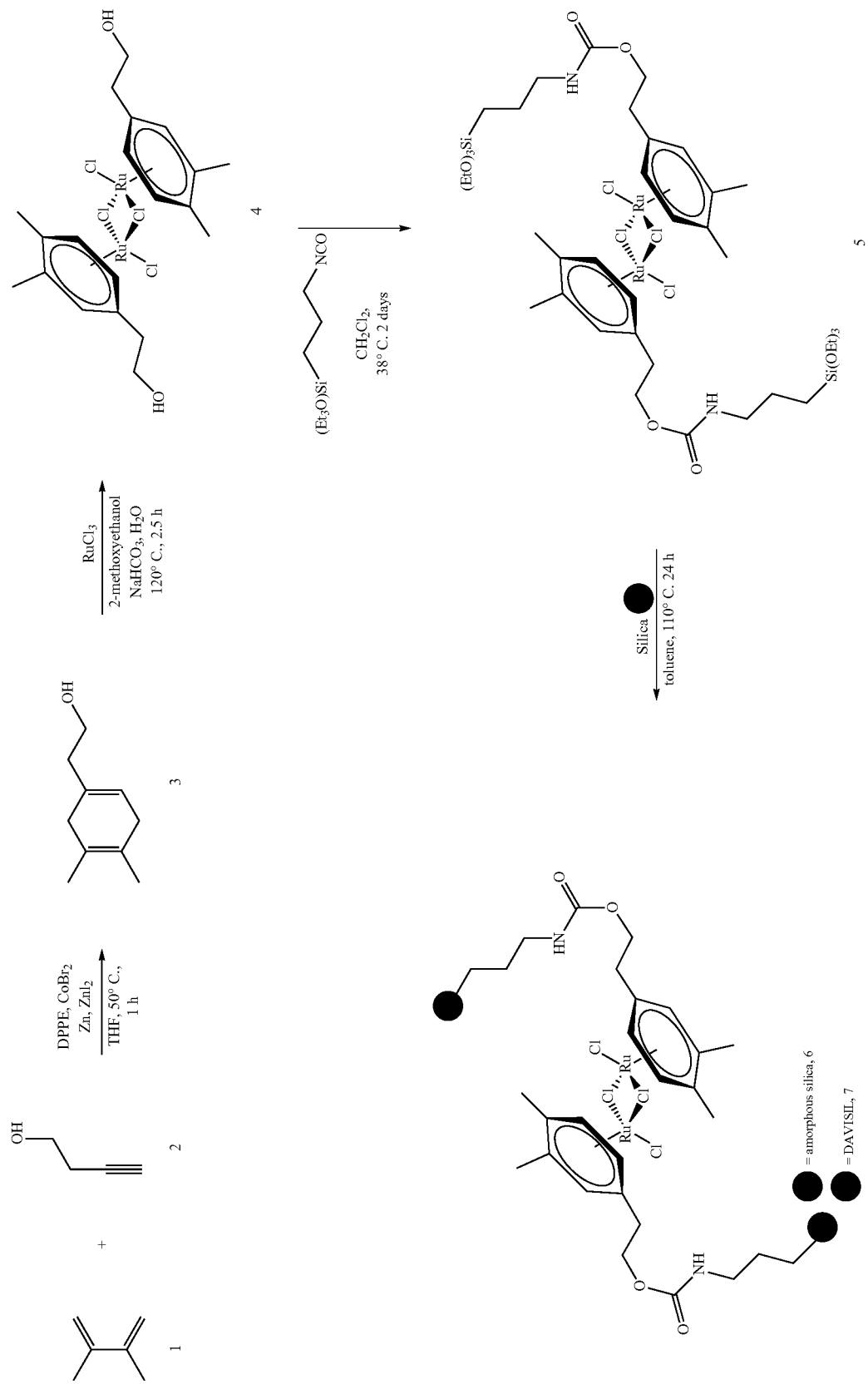
Scheme 1 Synthesis of silica-supported (arene)Ru(II) dimer 6 and 7.

Scheme 1. Synthesis of Silica-Supported (Arene)Ru(I) Dimers 6 and 7.

Our interest in anchoring (arene)Ru(Ih) to silica through the η6-coordinated arene was to develop a practical system that was amenable to diversification into a library of heterogeneous catalysts by modification with a range of ligands. With the aim of demonstrating the practicality of this approach, we chose to prepare Noyori-Ikariya-type precatalysts by reacting 6 and 7 with (S,S)-TsDPEN and evaluating their efficacy in the ATH of ketones. While it would be most convenient and cost effective to generate the catalyst in situ immediately prior to catalysis, precatalysts 8 and 9 were also first prepared on a large scale to accurately determine the ruthenium loading. Reactions were conducted in dichloromethane by stirring either 6 or 7 with a slight excess of (1S,2S)-TsDPEN and triethylamine for 4 h, in a modification of a previously reported procedure (Scheme 2). [124a] Precatalysts 8 and 9 were isolated as pale orange solids by filtration and the ruthenium content determined to be 0.021 and 0.032 mmol g-1, respectively, by ICP-OES giving loadings of 0.21 and 0.32 wt %. The solid state $^{13}$C cross-polarization magic angle spinning NMR spectra of 8 and 9 confirmed incorporation of the (arene)Ru(II)/TsDPEN precatalyst as signals between δ 4 and 51 ppm are characteristic of the SiCH$_2$, the CH$_2$ fragments of the aliphatic linker and the CH$_3$ substituents on the η6-arene ring and the TsDPEN, while those at δ 64 and 75 ppm correspond to the NCHPh carbon atoms of TsDPEN and the OCH$_2$ of the carbamate linker and those between δ 120 and 145 ppm belong to the carbon atoms of the aromatic ring of the TsDPEN and the η6-arene. Moreover, the chemical shifts of the structurally relevant carbon atoms map closely to those for the homogeneous molecular benchmark 10, further confirmation for incorporation of the (arene)Ru(II)/TsDPEN precatalyst. The magic angle spinning solid state $^{29}$Si spectra of 8 and 9 both contained two groups of signals typical for silica; a Q-series for inorganic silica (HO)nSi(OSi)$_{4-n}$ and a T-series for organic silica RSi(OSi)$_3$. The Q series appears as a set of three poorly resolved signals at ca. δ–91, –102 and –112 ppm for Q2 ((HO)2Si(OSi)$_2$), Q3 ((HO)Si(OSi)$_3$) and Q4 (Si(OSi)$_4$), respectively, and is markedly more intense than the major T3 species which is a broad ill-defined peak at δ–66 ppm (FIG. 2b); the disparate intensities of these resonances confirms that these catalysts are comprised mainly of inorganic silicate together with a minor amount of organic silicate resulting from immobilization of the silylated (arene)Ru(II)/TsDPEN on the walls of the silicate network. The X-ray photoelectron spectra of 8 and 9 each contained a doublet with binding energies of 462.28 eV (Ru 3p$_{1/2}$) and 484.58 eV (Ru 3p$_{3/2}$), and 463.78 eV (Ru 3p$_{1/2}$) and 486.68 eV (Ru 3p$_{3/2}$), respectively; these values are consistent with a Ru(II) species immobilized on the surface of silica.

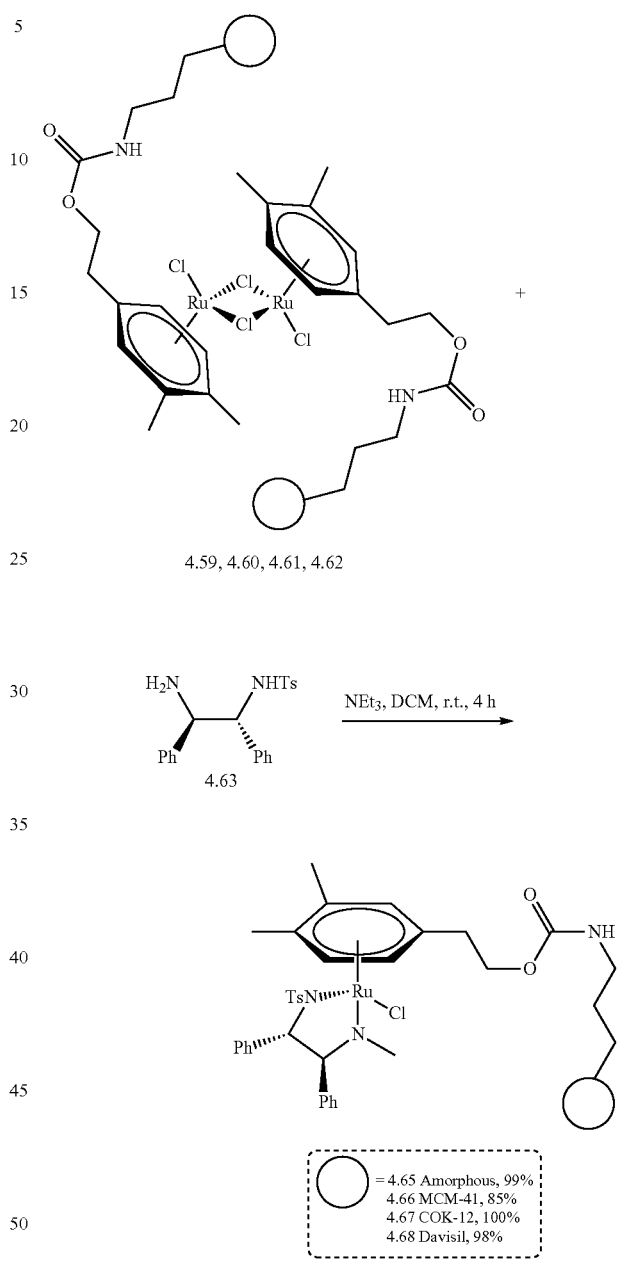

Scheme 2 Synthesis of silica-supported (areneRu(II)/TsDPEN precatalysts 8 and 9.

4.59, 4.60, 4.61, 4.62

= 4.65 Amorphous, 99%
4.66 MCM-41, 85%
4.67 COK-12, 100%
4.68 Davisil, 98%

Scheme 2. Synthesis of Silica-Supported (Arene)Ru(II)/TsDPEN Precatalysts 8 and 9.

Figure 3:
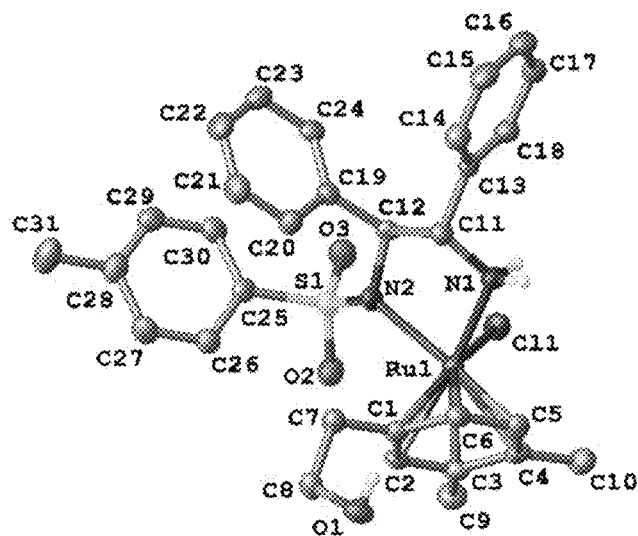
FIG. 3. Crystal structure of [(2-(3,4-dimethylphenyl) ethan-1-ol)Ru{(1S,2S)-TsDPEN}(Cl)] (10). Hydrogen atoms have been omitted for clarity with the exception of those bound to heteroatoms. Ellipsoids are drawn at the 50% probability level.

While it is conventional to undertake comparative catalyst testing against [(p-cymene)Ru{(1S,2S)-TsDPEN}Cl] as a soluble monomeric homogeneous pe-catalyst we chose to use [(2-(3,4-dimethylphenyl)ethan-1-ol)Ru{(1S,2S)-TsDPEN}(Cl)] (10) as it more closely represents a molecular analogue of 8 and 9 and, as such, should provide a more realistic assessment of the influence on catalyst performance of attachment to the support. Precatalyst 10 was prepared by stirring a dichloromethane solution of 4, (1S,2S)-TsDPEN and triethylamine for 1 h at RT. Although the NMR spectra, the electrospray mass spectrum and analytical data were all consistent with the formulation of 10, its identity was conclusively established by a single-crystal X-ray study; a perspective view of the molecular structure is shown in FIG. 3. The molecular structure shows that the crystal used to collect the data contains a single diastereoisomer which is consistent with the NMR spectroscopic data as there is no evidence for the presence of multiple species in either the 1H or 13C{1H}NMR spectra; however, this is not conclusive as resonances may be coincident or other diastereoisomers may be present but only as a minor component. FIG. 3 shows that the ruthenium atom adopts a piano stool pseudo-octahedral geometry with the η6-arene, chloride and the (1S,2S)-DPEN completing the coordination sphere. The Ru—C(arene) bond lengths fall in the range 2.162(5)-2.217(5) Å which is consistent with those reported for related complexes such as [(p-cymene)Ru{(1S,2S)-TsDPEN}(Cl)] (range: 2.141(7)-2.239(8) Å; mean: ca. 2.19 Å),[29] [{1,4-$C_6H_4$(Me)($C_4H_8$OH)}Ru{(1S,2S)-TsDPEN(Cl)](range: 2.166(3)-2.236(3) Å; mean: ca. 2.20 Å),[30] and [{$C_6H_5$($OCH_2CH_2$OH)}Ru{(1S,2S)-TsDPEN}(Cl)] (range: 2.18(2)-2.23(2) Å; mean: ca. 2.2 Å).[31] The Ru—N(1) and Ru—N(2) bond lengths of 2.104(5) Å and 2.162(4) Å, respectively, are also unexceptional and similar to those in this representative selection of precatalysts.

Asymmetric Transfer Hydrogenation of Ketones

Figure 4:
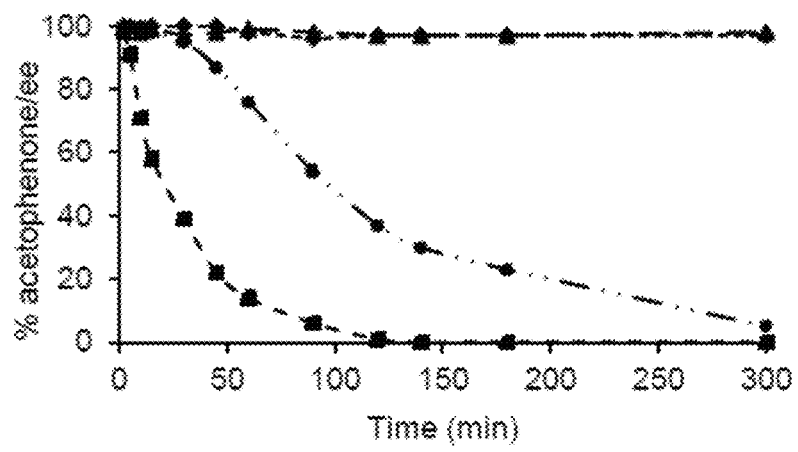
FIG. 4. Reaction profile as a function of time for the asymmetric transfer hydrogenation of acetophenone in neat HCOOH/NEt$_3$ azeotrope using (a) 0.17 mol-% 9 (% conversion ■ and % ee ▲) and (b) 0.17 mol-% 10 (% conversion ● and % ee ♦).

Preliminary catalyst screening and optimization focused on acetophenone as the substrate of choice as this is often employed as the benchmark for evaluating new catalysts; optical purity and yields were determined by GC analysis and full details are listed in Table 1. Reactions were initially conducted using catalyst generated in situ by reaction of either 6 or 7 with a slight excess of (S,S)-TsDPEN and triethylamine in dichloromethane for 1 h at 55° C., prior to addition of the reducing agent and substrate; comparative testing was also undertaken with pre-prepared catalysts 8 and 9. Table 1 shows that catalysts generated from either 6 or 7 and (S,S)-TsDPEN gave TOFs and ee's that either matched or outperformed those obtained with their soluble molecular counterpart 10, after 1.5 h at 55° C. using formic acidtriethylamine azeotrope as the hydrogen donor (Table 1, entries 1-2 and 5). Moreover, the ee's and yields obtained with both silicasupported systems match those reported for catalyst generated from [(p-cymene)Ru{(S,S)-TsDPEN}(Cl)] and triethylamine at a reaction temperature of 60° C.,[2b] and either compete with or outperform existing silica-supported (arene)Ru/TsDPEN-based catalysts immobilized through the nitrogen atom of the TsDPEN ligand, including magnetically retrievable mesoporous silica microcapsules[6c,6h] and (arene)Ru/TsDPEN confined in amphiphilic-modified nanocages of SBA-16,[32a,b] or supported on silica gel, mesoporous MCM-41, SBA-15,[6e,6d,6f,6g] or siliceous mesocellular foam (SMF).[6h,6i] Reassuringly, the ee's and TOF's obtained with preformed catalysts 8 and 9 also match those obtained with catalyst generated in situ which suggests that in situ formation of the catalyst under these conditions is efficient and essentially quantitative (Table 1, entries 3 and 4). The slightly higher yield obtained with 9 compared to 8 is most likely due to the increased efficiency in ruthenium loading, however, at this early stage, speculation as to the origin of minor differences in activity between catalyst supported on amorphous silica and DAVISIL® is not warranted. However, DAVISIL®-supported 9 was identified as the system of choice to undertake further studies and substrate screening (vide infra) as the more tightly controlled chemical and structural properties of DAVISIL silicas will enable a systematic investigation of the influence of the support on catalyst efficacy to be conducted. A survey of catalysts generated in situ by addition of various chiral diamines and amino alcohols including (S,S)-TsDPEN, (R,R)-Ph-pyBOX, (1R,2S)-1-amino-2-indanol and (S,S)-TsCYDN revealed (S,S)-TsDPEN generated the most efficient catalyst. Following this, precatalyst 9 was used to further explore the influence of varying reaction conditions and reagents on catalyst performance including solvent, temperature, time, catalyst loading and hydrogen donor. Variation of the hydrogen donor revealed that formic acid-triethylamine azeotrope gave the best combination of TOF and ee whereas $NaBH_4$ and $Me_2NHBH_3$ both gave near quantitative yields but very poor ee's and formate salts gave negligibly low conversions. As expected, lowering the reaction temperature resulted in a reduction in activity such that a conversion of 46% was reached at 50° C. with a slight improvement in the ee to 98%; the conversion could be improved by extending the reaction time with no loss in ee. Lowering the reaction temperature further to 45° C. resulted in a marked reduction in conversion to 18% after 1.5 h which increased to 81% after 5 h, in both cases with an ee of 98%. Finally, at 25° C. a reaction time of 24 h was required to reach 50% conversion with an ee of 98%; although more sluggish than reactions conducted at higher temperatures, the enantioselectivity and TOF were comparable to those obtained by Noyori using 0.5 mol-% [(η6 mesitylene)Ru{(S,S)-TsDPEN)(Cl)] as precatalyst.[2b] A reduction in the catalyst loading to 0.17 mol-% resulted in a slightly lower conversion of 77% with an enantioselectivity of 97% while a further reduction in the loading to 0.085 mol-% gave a much lower conversion of 26% but with an enantioselectivity of 99%. As there have been several reports of efficient ATH of ketones and imines in water using catalysts generated from silica-supported TsDPEN [6c,6d,6h,32a,b] a series of reactions were conducted in water, ethanol and methanol; however, in each case conversions were either low or negligible and, as such, all further reactions were performed in neat $HCOOH-NEt_3$ azeotrope. A study of the conversion and ee as a function of time using 0.17 mol-% 9 in neat $HCOOH/NEt_3$ azeotrope at 50° C. revealed that complete conversion was achieved after 2 h, which corresponds to an initial TOF of 1085 h-1 (FIG. 4, conversion, represented by a filled in square "■" and ee, represented by a filled in triangle "▲"). For comparison, the corresponding conversion-time profile using 0.17 mol-% 10 gave a markedly lower initial TOF of 260 h-1 (FIG. 4, conversion, represented by a filled in circle "●" and ee, represented by a filled in diamond "♦").

TABLE 1

Asymmetric transfer hydrogenation of acetophenone using precatalysts generated from silica-supported ruthenium dimers 6 and 7 their precatalysts 8 and 9 or molecular precatalyst 10.[a]

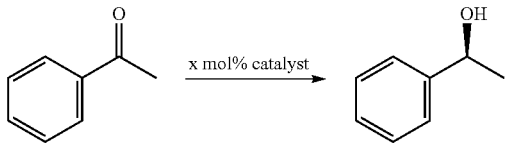

| Entry | Catalyst system | H-donor | Mol-% cat | Temp (° C.) | Solvent | Conv. % (TOF (h-1))[b] | ee (%)[b,c] |
|---|---|---|---|---|---|---|---|
| 1 | (S,S)-TsDPEN/6 | HCO$_2$H/NEt$_3$ | 0.22 | 55 | — | 90 (27) | 96 |
| 2 | (S,S)-TsDPEN/7 | HCO$_2$H/NEt$_3$ | 0.34 | 55 | — | 99 (194) | 97 |
| 3 | 8 | HCO$_2$H/NEt$_3$ | 0.22 | 55 | — | 88 (26) | 97 |
| 4 | 9 | HCO$_2$H/NEt$_3$ | 0.34 | 55 | — | 98 (19) | 97 |
| 5 | 10 | HCO$_2$H/NEt$_3$ | 1.00 | 55 | — | 99 (66) | 96 |
| 6 | (R,R)-Ph-pyBOX/7 | HCO$_2$H/NEt$_3$ | 0.34 | 55 | — | 2 (3) | nd |
| 7 | HCO$_2$H/(1R,2S)-1-amino-2-indanol/7 | HCO$_2$H/NEt$_3$ | 0.34 | 55 | — | 3 (6) | nd |
| 8 | (S,S)-TsCYDN/7 | HCO$_2$H/NEt$_3$ | 0.34 | 55 | — | 49 (96) | 90 |
| 9 | 9 | HCO$_2$H/NEt$_3$ | 0.17 | 55 | — | 77 (392) | 97 |
| 10 | 9 | Me$_2$NHBH$_3$ | 0.17 | 55 | — | 99 (388) | 7 |
| 11 | 9 | NaBH$_4$ | 0.17 | 55 | water | 98 (384) | 3 |
| 12 | 9 | KO$_2$CH | 0.17 | 55 | water | 5 (20) | 91 |
| 13 | 9 | NH$_4$O$_2$CH | 0.17 | 55 | water | 0 (0) | nd |
| 14 | 9 | HCO$_2$H | 0.17 | 55 | — | 0 (0) | nd |
| 15 | 9 | HCO$_2$H/NEt$_3$ | 0.085 | 55 | — | 26 (203) | 99 |
| 16 | 9 | HCO$_2$H/NEt$_3$ | 0.17 | 15 | — | 46 (180) | 98 |
| 17 | 9 | HCO$_2$H/NEt$_3$ | 0.17 | 45 | — | 18 (71) | 98 |
| 18[d] | 9 | HCO$_2$H/NEt$_3$ | 0.17 | 25 | — | 50 (12) | 98 |
| 19 | 9 | HCO$_2$H/NEt$_3$ | 0.17 | 55 | water | 0 (0) | nd |
| 20 | 9 | HCO$_2$H/NEt$_3$ | 0.17 | 55 | EtOH | 14 (55) | 49 |
| 21 | 9 | HCO$_2$H/NEt$_3$ | 0.17 | 55 | MeOH | 12 (47) | 54 |

[a]Reactions were carried out with 0.5 mmol of acetophenone using precatalyst generated from silica-supported ruthenium dimers 6 and 7 or pre-prepared silica supported (arene)Ru/TsDPEN precatalysts 8, 9 or 10 in neat HCOOH-NEt$_3$ azeotrope for 90 min (unless otherwise stated) under the specified conditions of temperature, S/C ratio, hydrogen donor and solvent.
[b]Determined by gas chromatography equipped with a CP-Chirasil-DEX CB column using decane as internal standard.
[c]Configuration was determined to be S from the sign of the optical rotation.
[d]Reaction time of 24 h.

The improved performance of 9 compared with 10 could be due to either 'confinement', [133] site isolation [134] or preorganization of the C—H/π interaction arising from attachment of the η6-arene ring to the silica [4m,35] and further catalyst modifications are currently underway to explore the origin of this enhancement. Gratifyingly, the TOF obtained with 9 also appears to be significantly higher than Noyori-Ikariya catalysts immobilized on mesoporous silica, [6f,6h-i,7g,9a,32b] polystyrene, [7b,7d,7f] or polyethylene glycol. [8a-c,9b] Based on the above screening study, a temperature of 50° C. and reaction time of 5 h was considered to be the best compromise to explore the substrate scope and efficacy of DAVISIL® silica supported 9.

Having identified optimum conditions and obtained encouraging conversions and ee's for the benchmark transfer hydrogenation of acetophenone, catalyst testing was extended to a range of aryl and heteroaryl ketones to explore and assess the scope and limitations of DAVISIL®-supported precatalyst 9 and its molecular counterpart 10 (Table 2). Good to excellent conversions and high ee's to the corresponding secondary alcohol were obtained across a range of electron deficient 2-, 3- and 4-substituted ketones (Table 2, entries 1-10) and in most cases, silica-supported 9 either rivalled or outperformed its molecular counterpart 10. Moreover, the TOFs and ee obtained with 9 are comparable to or better than those previously reported for (arene)Ru/TsDPEN precatalysts supported on mesoporous silica [6c, 6d,6e,6g] and siliceous mesocellular foam [6h,6i] and encapsulated within nanocages of amphiphilic SBA-16[32] as well as PEG-based polymers [8a,8b,8c,9b] and styrene-based systems such as a poly(styrene-1-phosphonate styrene) inorganic zirconium phosphate-phosphonate hybrid, [7a] phosphonate containing polystyrene copolymer,[7b] cross-linked polystyrene, [7d] and amphiphilic polystyrene. [7f] While high ee's were obtained with each of the 4-substituted acetophenones examined, the ee's obtained with their 2-substituted counterparts were more disparate and varied between 87-98%. For example, reduction of 2-bromoacetophenone gave 1-(2-bromophenyl)ethan-1-ol with an ee of 98% whereas its 2-chloro-substituted counterpart gave the corresponding secondary alcohol in 87% ee. High conversions and excellent ee's were also obtained for arylketones substituted with electron donating groups at the 2-, 3- and 4-positions (Table 2, entries 11-13) as well as 2-acetonaphthone (Table 2, entry 14) all of which gave the corresponding alcohol in 99-100% ee. Even though the p-methoxyacetophenone only reached 60% conversion after 5 h under these conditions (Table 2, entry 11), the ee of 99% is an improvement on that reported for [(η6-mesitylene)Ru{(S,S)-TsDPEN}CL][2b] as well as the majority of silica, [6]

polymer [7,14] and PEG-supported [8] catalysts; moreover, complete conversion was obtained by extending the reaction time to 12 h with no loss in ee. The same protocol was extended to the asymmetric transfer hydrogenation of 2-acetylfuran and 2-acetylthiophene which gave 91% and 78% conversion to (S)-1-(2-furyl)ethanol and (S)-1-(2-thienyl)ethanol, respectively, both with 100% ee (Table 2, entries, 15 and 16).

Figure 5:
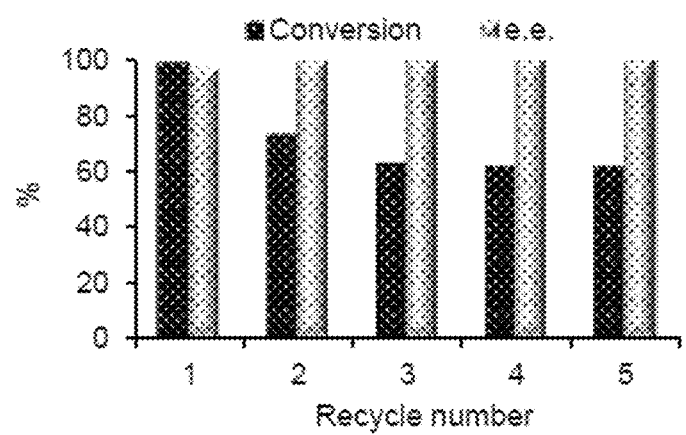
FIG. 5. Recycle study for the transfer hydrogenation of acetophenone using precatalyst 9 and a reaction time of 4 h.

While 9 tolerated the steric hindrance of a variety of orthosubstituted acetophenones, negligible conversions were obtained with 2,2-dimethyl-1-phenylpropan-1-one, 1-tetralone, 1-acetonaphthone, and cyclopropyl(phenyl)methanone, which are sterically much more demanding substrates. Unfortunately, 9 was also unable to reduce 3- and 4-acetylpyridine as quantitative amounts of starting material were consistently recovered even after an extended reaction time of 10 h. Reasoning that the presence of a large excess of nitrogen donor could result in ligand substitution of either the TsDPEN or chloride and afford a less active or inactive pyridine-saturated species, pre-treatment of a mixture of 0.17 mol-% 9 and $HCO_2H/NEt_3$ azeotrope with 0.5 mmol of 3-acetylpyridine at 50° C. for 15 min resulted in a significant reduction in activity as a conversion of only 14% with an ee of 98% was obtained for the reduction of acetophenone, compared with complete conversion and an ee of 98% under the same conditions but in the absence of 3-acetylpyridine. In a modification of this investigation, the conversion of acetophenone as a function of 3-acetylpyridine addition time was investigated by running a series of hydrogenations in parallel and adding 3-acetylpyridine after 0.5 h, 1 h and 2 h and working each reaction up after 5 h; the conversion profile of 54% (0.5 h), 81% (1 h) and 98% (2 h) shows that addition of 3-acetylpyridine results in near instantaneous deactivation of the catalyst as the conversions obtained at each time interval are similar to those obtained for the same reaction in the absence of 3-acetylpyridine. In a scale-up experiment, the asymmetric transfer hydrogenation of 2-bromoacetophenone on a 10 mmol scale in 5.0 mL of the $HCO_2H/NEt_3$ azeotrope gave complete conversion to 1-(2-bromophenyl)ethan-1-ol with an ee of 98% after 9 h at 50° C. The reusability of 9 was investigated for the benchmark transfer hydrogenation of acetophenone under the conditions described above to assess the robustness and longevity of the catalyst and the potential for integration into a continuous flow reactor set-up. Recycle experiments were conducted on a larger scale to try and overcome the practical problems associated with recovering the catalyst from a small-scale reaction. Reactions were run for 4 h to avoid complete conversion which would enable any change in activity to be observed. The catalyst was recycled by quenching the reaction with a large excess of ethyl acetate, recovering the catalyst by centrifugation, and removing the organic phase with a syringe, then recharging the flask with additional portions of $HCO_2H/NEt_3$ azeotrope and acetophenone. [7d] Following this protocol, 9 gave consistently high ee's (>99%) across five cycles although conversions dropped gradually from 99% in the first run to 77% and 63% in the second and third runs, respectively, after which they remained constant (FIG. 5). ICP analysis of the organic phase collected during the first three runs revealed leaching of the ruthenium to be the primary reason for the decrease in conversion as the ruthenium content dropped by 18% in run 1 and 8% and 5% in runs 2 and 3, respectively, which closely correlates with the reduction in conversion. To this end, Hintermair has recently provided convincing evidence for two deactivation/inhibition pathways for (arene)(TsDPEN)Ru—H, one of which involves gradual dissociation of the arene ligand while the other involves competitive inhibition of the unsaturated intermediate by excess base. [36] Even though the activity dropped during the first two runs, the stable activity profile during successive runs suggests that the remaining supported ruthenium sites are robust with respect to leaching and/or deactivation and inhibition.

Table 2. Asymmetric Transfer Hydrogenation of Ketones in Formic Acid-Triethylamine Azeotrope using Silica-Supported Precatalyst 9 and Molecular Precatalyst 10. [a]

| Entry | Substrate | Precatalyst 9 Conv(%)/TOF $(h^{-1})$)[b] | ee (%)[b,c] | Precatalyst 10 Conv(%)/TOF $(h^{-1})$)[b] | ee (%)[b,c] |
|---|---|---|---|---|---|
| 1 | 4-bromoacetophenone | 100 (118) | 93 | 95 (112) | 92 |
| 2 | 2-bromoacetophenone | 99 (116) | 98 | 100 (118) | 75 |
| 3 | 4-fluoroacetophenone | 91 (107) | 94 | 100 (118) | 94 |

| | | Precatalyst 9 | | Precatalyst 10 | |
|---|---|---|---|---|---|
| Entry | Substrate | Conv(%)/TOF (h$^{-1}$))$^b$ | ee (%)$^{b,c}$ | Conv(%)/TOF (h$^{-1}$))$^b$ | ee (%)$^{b,c}$ |
| 4 | 3-F-C6H4-C(O)CH3 | 100 (118) | 94 | 100 (118) | 95 |
| 5 | 2-F-C6H4-C(O)CH3 | 100 (118) | 92 | 100 (118) | 80 |
| 6 | 2-Cl-C6H4-C(O)CH3 | 80 (92) | 87 | 95 (112) | 83 |
| 7 | 4-Cl-C6H4-C(O)CH3 | 100 (118) | 96 | 100 (118) | 93 |
| 8 | 3-O2N-C6H4-C(O)CH3 | 100 (118) | 80 | 98 (115) | 79 |
| 9 | 4-O2N-C6H4-C(O)CH3 | 99 (116) | 97 | 96 (113) | 97 |
| 10 | 3-F3C-C6H4-C(O)CH3 | 99 (116) | 93 | 100 (118) | 93 |
| 11 | 4-MeO-C6H4-C(O)CH3 | 60 (71) | >99 | 90 (106) | >99 |
| 12 | 2-MeO-C6H4-C(O)CH3 | 100 (118) | >99 | 100 (118) | >99 |

-continued

| Entry | Substrate | Precatalyst 9 | | Precatalyst 10 | |
|---|---|---|---|---|---|
| | | Conv(%)/TOF (h$^{-1}$))[b] | ee (%)[b,c] | Conv(%)/TOF (h$^{-1}$))[b] | ee (%)[b,c] |
| 13 | MeO-C6H4-C(O)CH3 (3-methoxyacetophenone) | 98 (115) | 99 | 99 (116) | 99 |
| 14 | 2-acetonaphthone | 100 (118) | 97 | 100 (118) | 98 |
| 15 | 2-acetylfuran | 91 (107) | 100 | 95 (112) | 99 |
| 16 | 2-acetylthiophene | 78 (92) | 100 | 88 (103) | 97 |

CONCLUSION

In conclusion, this paper describes the first example of a Noyori-Ikariya precatalyst anchored to amorphous silica and DAVISIL by immobilization through the η6-coordinated arene ligand, which was prepared via a cobalt-catalyzed [4+2] cycloaddition between a homopropargylic alcohol and a diene. The derived catalysts (arene)Ru(II)/TsDPEN@silica and (arene)Ru(II)/TsDPEN@DAVISIL® exhibit excellent activity for the asymmetric transfer hydrogenation of a range of electron-rich and electron-poor aromatic ketones, giving good conversions and high ee's under mild reaction conditions. Catalyst generated in situ, by reaction of the corresponding silica-supported (arene)Ru(II) dimer with (S,S)-TsDPEN immediately prior to addition of substrate and hydrogen donor, either competed with or outperformed its preformed counterpart [(arene)Ru{(S,S)-TsDPEN)Cl]@silica, which presents numerous practical advantages for catalyst optimization, substrate screening and reaction diversification. Gratifyingly, the TOFs and ee's obtained with these catalysts rivalled those previously reported for catalysts immobilized on either silica or polymer through a nitrogen atom of the Ts-DPEN ligand. High ee's were maintained during recycle studies.

Experimental Section

Synthesis of 2-(4,5-Dimethylcyclohexa-1,4-dien-1-yl)ethan-1-ol (3)

According to the literature method, [24b] Zn powder (0.28 g, 4.22 mmol), ZnI$_2$ (1.40 g, 4.38 mmol), CoBr$_2$ (0.48 g, 2.19 mmol), and DPPE (0.86 g, 2.15 mmol) were added to a three-neck flask (250 mL) and stirred in dry THF (30 mL) at room temperature. 1,3-Dimethyl-butadiene (13.5 mL, 118 mmol) was added to the reaction mixture after 5 minutes, followed by but-3-yn-1-ol (7.9 mL, 105 mmol). The resulting mixture was stirred for 5 mins and then heated to 50° C. for one hour, after which the solvent was removed under reduced pressure. The crude mixture was purified by vacuum distillation (1 mmHg, 115-121° C.) to afford diene 3 in 63% yield (10.1 g). 1H NMR (300 MHz, CDCl$_3$, δ): 5.49-5.41 (m, 1H, =CH), 3.70-3.53 (m, 2H. CH$_2$OH), 2.63-2.39 (m, 4H, CH$_2$), 2.21-2.14 (m, 2H, CH$_2$CH$_2$OH), 1.60 (s, 6H, CH3). 13C{1H} NMR (75 MHz, DMSO, δ): 104.1, 102.6, 95.8, 87.5, 87.2, 83.4, 60.4, 36.2, 16.9, 16.3.

Synthesis of [RuCl$_2${2-(3,4-dimethylphenyl)ethan-1-ol}]2 (4)

According to the literature, [37] a suspension of RuCl$_3$.H$_2$O (1.1 g, 5.3 mmol) and NaHCO$_3$(0.45 g, 5.3 mmol) in a mixture of 2-methoxyethanol:H$_2$O (11 mL, 10:1) was added 2-(4,5-dimethylcyclohexa-1,4-dien-1-yl)ethan-1-ol 3 (3.2 g, 21.2 mmol). The resulting mixture was heated at 120° C. for 2.5 h after which time half of the solvent was removed under reduced pressure and diethyl ether added (10 mL) to precipitate an orange solid. The solid was filtered, washed with Et$_2$O and dried to obtain the dimer 4 as an orange powder in 49% yield (0.9 g). 1H NMR (300 MHz, DMSO, δ): 5.81 (d, J=5.6 Hz, 1H, ArH), 5.70 (s, 1H, ArH), 5.58 (d, J=5.6 Hz, 1H, ArH), 4.76 (t, J=5.1 Hz, 1H, OH), 3.68 (qd, J=6.5, 3.3 Hz, 2H, CH$_2$OH) 2.65-2.53 (m, 1H, CHaCHbCH$_2$OH), 2.47-2.34 (m, 1H, CHaCHbCH$_2$OH), 2.05 (s, 3H, CH3), 1.96 (s, 3H, CH$_3$). 13C{1H} NMR (75 MHz, DMSO, δ):104.1, 102.7, 95.7, 87.5, 87.2, 83.3, 60.4, 36.2, 17.0, 16.3. IR: δ max cm-1 735, 863, 899, 1023, 1044, 1081, 117, 1211, 1297, 1377, 1438, 2858, 2914, 3039, 3429 (br). HRMS (ESI) calculated for C12H17O3Ru [Ru(arene)OAc]+: 311.0220, Found: 311.0217.

Synthesis of [RuCl2 O-(3,4-dimethylphenethyl N-(3-(triethoxysilyl)propyl) carbamate)]2 (5)

In a modification of a previously reported literature procedure, [24a] 3-(triethoxysilyl)propyl isocyanate (0.26 mL, 1.1 mmol) was added to [RuCl$_2$(2-(3,4-dimethylphenyl)ethan-1-ol)]2 (0.456 g, 0.70 mmol) and NEt$_3$ (0.49 mL, 3.54 mmol) in dry dichloromethane (10 mL). The reaction mixture was heated to 38° C. for 48 h. The solvent was removed under reduced pressure to obtain a brown oil which was triturated with hexane (2×10 mL). The resulting crude oil (0.645 g, 77%) was re-dissolved in dry dichloromethane (10 mL) to give a dark red solution which was used without further purification. 1H NMR (300 MHz, CDCl$_3$, δ): 5.28-4.82 (m, 3H, Ar—H), 4.38-4.11 (m, 2H, CH$_2$CH$_2$O), 3.84-3.64 (m, 6H, (CH$_3$CH$_2$O)3Si), 3.15-2.97 (m, 2H, CH$_2$NH) 2.90-2.69 (m, 2H, C$_6$H$_3$—CH$_2$CH$_2$O), 2.19-2.06 (m, 3H, CH$_3$). 2.07-1.99 (m, 3H, CH$_3$) 1.62-1.43 (m, 2H, NHCH$_2$CH$_2$CH$_2$), 1.21-1.07 (m, 9H, (CH$_3$CH$_2$O) 3Si), 0.60-0.43 (m, 6H, CH2Si). IR: □max cm-1 3264, 2973, 2927, 2882, 1682, 1254, 1069, 951, 768. HRMS (ESI) calculated for C$_{20}$H$_{35}$O$_5$NClRuSi, [Ru(arene)Cl]+: 534.1011, found: 534.1011.

Synthesis of Silica-Supported Ruthenium Dimers 6 and 7

A two-necked flame-dried round bottom flask was charged with 5 (4.88% w/w solution in dichloromethane; 6 mL, containing 0.34 mmol of Ru), the solvent was removed under reduced pressure and toluene (6 mL) added. Amorphous silica or DAVISIL® (7.10 g) was then added to the solution and the mixture was heated to 110° C. with rapid stirring for 24 h. After this time the mixture was left to cool and the solid was filtered, washed with ethyl acetate (3×10 mL) and dried at 45° C. overnight to afford 6 and 7 as orange solids in 93% (7.45 g) and 99% (7.49 g) yield, respectively. ICP-OES data for 6: 0.23 wt % ruthenium corresponding to a ruthenium loading of 0.023 mmol g-1. ICP-OES data for 7: 0.37 wt % ruthenium corresponding to a ruthenium loading of 0.037 mmol g-1.

Synthesis of Silica-Supported [{2-(3,4-Dimethylphenylethyl propyl carbamate)}Ru[(S,S)-TDPEN)Cl] Precatalysts 8 and 9

In a typical procedure, triethylamine (0.094 mL, 0.68 mmol), silica-supported ruthenium dimer 6 or 7 (mass corresponding to 0.34 mmol of Ru calculated from the ruthenium loading) and (S,S)-TsDPEN (0.155 g, 0.42 mmol) were stirred in dichloromethane (20 mL) for 4 h at room temperature after which time the solid was filtered, washed with dichloromethane (3×5 mL) and dried in an oven at 40° C. for 5 h to obtain silica-supported precatalysts 8 and 9 as orange solids in 99% (3.7 g) and 98% (3.7 g) yield, respectively. ICP-OES data for 8: 0.21 wt % ruthenium corresponding to a ruthenium loading of 0.021 mmol g-1. ICP-OES data for 9: 0.32 wt % ruthenium corresponding to a ruthenium loading of 0.032 mmol g-1.

Synthesis of RuCl(S,S)-TsDPEN[(2-(3,4-dimethylphenyl)ethan-1-ol] (10)

In a modification of a previously reported literature procedure, [24a] (S,S)-TsDPEN (0.100 g, 0.28 mmol), 4 (0.089 g, 0.14 mmol) and triethylamine (0.056 g, 0.55 mmol) were dissolved in dichloromethane (3 mL) and the reaction mixture was stirred at room temperature for 1 h. The resulting orange solid was filtered, washed with dichloromethane (1 mL) and dried to obtain precatalyst 10 as an orange solid (0.103 g, 56%). 1H NMR (300 MHz, DMSO, δ): 7.24-7.32 (m, 1H, NH), 7.14-7.06 (m, 5H, ArH+NH), 6.83-6.54 (m, 10H, ArH), 5.74 (s, 1H, ArH), 5.62-5.59 (m, 1H, ArH), 5.44-5.43 (m, 1H, ArH), 4.91-4.89 (m, 1H, OH), 3.80-3.75 (m, 2H, CH$_2$OH), 3.62-3.60 (m, 1H, CHNTs), 3.16-3.10 (m, 1H, CHN), 2.92-2.86 (m, 1H, CHaHbCH$_2$OH), 2.69-2.64 (m, 1H, CHaHbCH$_2$OH), 2.22 (s, 3H, Me), 2.20 (s, 3H, Me), 2.08 (m, 3H, Me). 13C{1H} NMR (75 MHz, DMSO, δ): 143.7, 140.5, 140.2, 138.6, 129.3, 128.5, 127.9, 127.9, 127.5, 127.5, 127.1, 126.4, 94.6, 94.4, 94.3, 88.7, 81.2, 79.4, 71.9, 69.3, 61.3, 36.7, 21.2, 17.1, 16.9. IR: δ max cm-1 535, 575, 695, 699, 813, 918, 1064, 1129, 1265, 1422, 1453, 1575, 2875, 2925, 3028, 3056, 3243, 3301, 3433 (br). HRMS (ESI) calculated for C31H35N2O3RuS [M-Cl]+: 611.1439; found: 611.1440. M.P.: 221-223° C.

ATH of Acetophenone and its Derivatives Using Preformed Silica-Supported Precatalysts 8 and 9.

Ketone (0.5 mmol) was added to a suspension of either 8 (0.22 mol-% Ru, 0.052 g, 0.0011 mmol) or 9 (0.34 mol-% Ru, 0.053 g, 0.0017 mmol) and 5:2 formic acid:triethylamine azeotrope (0.25 mL, 3.0 mmol of HCO$_2$H) in a flame-dried Schlenk tube and the mixture stirred at the specified temperature for the allocated time. The orange mixture was filtered through a short silica plug, washed through with diethyl ether (2×10 mL) and the solvent removed under reduced pressure. The residue was dissolved in CDC$_{13}$ (0.7 mL), decane (97 µL, 0.5 mmol) added as internal standard, and the solution analysed by 1H NMR spectroscopy and gas chromatography to determine the conversion and enantioselectivity.

ATH of Acetophenone Using In-Situ Generated Silica-Supported Precatalysts.

A flame-dried Schlenk flask was charged with silica-supported ruthenium dimer 6 (0.22 mol-%, 0.048 g, 0.0011 mmol) or 7 (0.34 mol-%, 0.046 g, 0.0017 mmol), ligand (1.3 equivalents based on ruthenium) and triethylamine (2.0 equivalents based on ruthenium) and the resulting suspension stirred for 1 h under nitrogen at 55° C. After this time, HCO$_2$H/NEt$_3$ (0.25 mL, 3.0 mmol of HCO$_2$H) and the ketone (0.5 mmol) were added and the mixture stirred at 55° C. for the allocated time, after which it was filtered through silica and washed through with diethyl ether (2×10 mL) and the solvent removed under reduced pressure. The residue was dissolved in CDCl$_3$ (0.7 mL), decane (97 µL, 0.5 mmol) was added as internal standard and the solution analysed by 1H NMR spectroscopy and gas chromatography to determine the conversion and enantioselectivity.

ATH of Acetophenone and its Derivatives Using Precatalyst 10.

A flame-dried Schlenk flask containing 5:2 formic acid:triethylamine (0.25 mL, 3.0 mmol of HCO$_2$H) and the ketone (0.5 mmol) was charged with precatalyst 10 (0.0036 g, 5.5 µmol, 1 mol %) and the resulting mixture stirred at 50° C. for 5 h. After this time, the resulting orange mixture was filtered through silica and flushed with diethyl ether (2×10 mL) and the solvent removed under reduced pressure. The residue was dissolved in CDCl$_3$ (0.7 mL) and decane (97 µL, 0.5 mmol) added as internal standard and the solution analysed by 1H NMR spectroscopy and gas chromatography to determine the conversion and enantioselectivity.

ATH of Acetophenone Using Precatalyst 10 Generated In-Situ from 4.

A Schlenk flask was charged with 5:2 formic acid:triethylamine (0.25 mL, 3.0 mmol of HCO$_2$H), 4 (0.0035 g, 5.0

μmol) and (S,S)-TsDPEN (2.8 mg, 7.6 μmol) and the mixture stirred at 55° C. for 15 min. After this time, acetophenone (0.058 mL, 0.50 mmol) was added and stirring continued for a further 90 min. The resulting orange mixture was filtered through silica and flushed through with diethyl ether (2×10 mL) and the solvent removed under reduced pressure. The residue was dissolved in CDCl3 (0.7 mL), decane (97 μL, 0.5 mmol) was added as internal and the solution analysed by 1H NMR spectroscopy and gas chromatography to determine the conversion and enantioselectivity.

General Procedure for Catalyst Recycling.

A centrifuge tube was charged with precatalyst 9 (0.17 mol %, 0.106 g, 0.0034 mmol), 5:2 formic acid:triethylamine (1.0 mL, 12.0 mmol of $HCO_2H$) and acetophenone (0.232 mL, 0.2 mmol) and the reaction mixture heated at 55° C. for 5 h under a nitrogen atmosphere. After this time water was added (1.0 ml) and the tube was placed in a centrifuge at 5000 rpm for 5 min and the formic acid:triethylamine carefully removed by pipette. Following this the solid was re-suspended in formic acid:triethylamine azeotrope and water, centrifugation repeated and the formic acid:triethylamine removed. After a third washing the solid was dried in vacuum before adding further portions of formic acid:triethylamine azeotrope and acetophenone. The combined aqueous washings were extracted with diethyl ether to obtain a sample for analysis by 1H NMR spectroscopy and gas chromatography.

X-Ray Crystallography

Crystal structure data were collected at 150 K on a Rigaku Oxford Diffraction Xcalibur, Altas, Gemini Ultra diffractometer using equipped with a sealed tube X-ray source (λ CuK α=1.54184 Å) and an Oxford CryostreamPlus open-flow $N_2$ cooling device. Intensities were corrected for absorption using a multifaceted crystal model created by indexing the faces of the crystal for which data were collected. [38] Cell refinement, data collection and data reduction were undertaken via the software CrysAlisPro. [39] All structures were solved using XT [40] and refined by XL [41] using the Olex2 interface. [42] All non-hydrogen atoms were refined as anisotropic and hydrogen atoms were positioned with idealized geometry, with the exception of those bound to heteroatoms, the positions of which were located using peaks in the Fourier difference map. The displacement parameters of the hydrogen atoms were constrained using a riding model with UH set to be an appropriate multiple of the Ueq value of the parent atom.

Deposition Numbers 2045014 (for 4) and 2045015 (for 10) contain the supplementary crystallographic data for this paper. These data are provided free of charge by the joint Cambridge Crystallographic Data Centre and Fachinformationszentrum Karlsruhe Access Structures service at the website located at ccdc.cam.ac.uk/structure.

REFERENCES

[1] a) M. J. Palmer, M. Wills, Tetrahedron: Asymmetry 1999, 10, 2045-2061; b) X. Wu, J. Xiao, Chem. Commun. 2007, 24, 2449-2466; c) H.-U. Blaser, C. Malan, B. Pugin, F. Spindler, H. Steiner, M. Studer, Adv. Synth. Catal. 2003, 345, 103-151; d) K. Everaere, A. Mortreux, J.-F. Carpentier, Adv. Synth. Catal. 2003, 345, 67-77; e) C. Saluzzo, M. Lemaire, Adv. Synth. Catal. 2002, 344, 915-928; f) Q.-H. Fan, Y.-M. Li, A. S. C. Chan, Chem. Rev. 2002, 102, 3385-3466.

[2] a) S. Hashiguchi, A. Fujii, J. Takehara, T. Ikariya, R. Noyori, J. Am. Chem. Soc. 1995, 117, 7562-7563; b) A. Fujii, S. Hashiguchi, N. Uematsu, T. Ikariya, R. Noyori, J. Am. Chem. Soc. 1996, 118, 2521-2522; c) K. Matsumura, S. Hashiguchi, T. Ikariya, R. Noyori, J. Am. Chem. Soc. 1997, 119, 8738-8739; d) K. Murata, K. Okano, M. Miyagi, H. Iwane, R. Noyori, T. Ikariya, Org. Lett. 1999, 1, 1119-1121.

[3] a) Y.-M. He, Q.-H. Fan, Org. Biomol. Chem. 2010, 8, 2497-2504; b) T. Touge, T, Arai, J. Am. Chem. Soc. 2016, 138, 11299-13105; c) T. Ohkuma, N. Utsumi, K. Tsutsumi, K. Murata, C. Sandoval, R. Noyori, J. Am. Chem. Soc. 2006, 128, 8724-8725; d) W. Ma, J. Zhang, C. Xu, F. Chen, Y.-M. He, Q.-H. Fa, Angew. Chem. Int. Ed. 2016, 55, 12891-12894; e) C. A. Sandoval, T. Ohkuma, N. Utsumi, K. Tsutsumi, K. Murara, R. Noyori, Chem.-Asian J. 2006, 1, 102-110; f) Z. Yang, F. Chen, Y. He, N. Yang, Q.-H. Fa, Angew. Chem. Int. Ed. 2016, 55, 13863-13866; g) T. Ohkuma, K. Tsutsumi, N. Utsumi, N. Arai, R. Noyori, K. Murata, Org. Lett., 2007, 9, 255-257; h) M. Ito, Y. Endo, T. Ikariya, Organometallics 2008, 27, 6053-6055; i) Z. M. Heiden, T. B. Rauchfuss, J. Am. Chem. Soc. 2009, 131, 3593-3600.

[4] For a highly informative and insightful review see: a) H. G. Nedden. A. Zanotti-Gerosa, M. Wills, Chem. Rec. 2016, 16, 2623-2643; For selected examples see: b) D. J. Cross, J. A. Kenny, I. Houson, L. Campbell, T. Walsgrove, M. Wills, Tetrahedron: Asymmetry 2001, 12, 1801-1806; c) F. K. Cheung, C. Lin, F. Minissi, A. L. Crivillé, M. A. Graham, D. J. Fox, M. Wills, Org. Lett. 2007, 9, 4659-4662; d) J. Wettergren, E. Buitrago, P. Ryberg, H. Adolfsson, Chem.-Eur. J, 2009, 15, 5709-5718; e) A. E. Cotman, D. Cahard, B. Mohar, Angew. Chem. Int. Ed. 2016, 55, 5294-5298; f) A. Kišić, M. Stephan, B. Mohar, Adv. Synth. Catal. 2015, 357, 2540-2546; g) T. Thorpe, A. J. Blacker, S. M. Brown, C. Bubert, J. Crosby, S. Fitzjohn, J. P. Muxworthy, J. M. J. Williams, Tetrahedron Lett. 2001, 42, 4041-4043; h) A. Schlatter, W.-D. Woggon, Adv. Synth. Catal, 2008, 350, 995-1000; i) W. Baratta, F. Benedetti, A. Del Zotto, L. Fanfoni, F. Felluga, S. Magnolia, E. Putignano, P. Rigo, Organometallics 2010, 29, 3563-3570; j) X. Wu, J. Xiao, Chem. Commun. 2007, 2449-2466; k) D. Šterk, M. S. Stephan, B. Mohar, Tetrahedron: Asymmetry 2002, 13, 2605-2608; l) R. Soni, K. E. Jolley, G. J. Clarkson, M. Wills, Org. Lett. 2013, 15, 5110-5113; m) V. Parekh, J. A. Ramsden, M. Wills, Catal. Sci. Technol. 2012, 2, 406-414.

[5] a) P. A. Bradley, R. L. Carroll, Y. C. Lecouturier, R. Moore, P. Noeureuil, B. Patel, J. Snow, S. Wheeler, Org. Process Res. Dev. 2010, 14, 1326-1336; b) R. Fu, J. Chen, L.-C. Guo, J.-L. Ye, Y.-P. Ruan, P.-Q. Huang, Org. Lett. 2009, 11, 5242-5245; c) G. Kumarasway, G. Ramakrishna, P. Naresh, B. Jagadeesh, B. Sridhar, J. Org. Chem. 2009, 74, 8468-8471; d) T. J. Greshock, D. M. Johns, Y. Noguchi, R. M. Williams, Org. Lett. 2008, 10, 613-616; e) Q. Zhang, B.-W. Ma, Q.-Q. Wang, X.-X. Wang, X. Hu, M.-S. Xie, G.-R. Qu, H.-M. Guo, Org. Lett. 2014, 16, 2014-2017; f) M. Hennig, K. Puntener. M. Scalone, Tetrahedron: Asymmetry 2000, 11, 1849-1858; g) Z. Ding, J. Yang, T. Wang, Z. Shen, Y. Zhang, Chem. Commun. 2009, 571-573; h) B. Zhang, M.-H. Xu, G.-Q. Lin, Org. Lett., 2009, 11, 4712-4715; i) G. Kumaraswamy, D. Rambabu, Tetrahedron; Asymmetry 2013, 24, 196-201; j) K. Leijondahl, A.-B. L. Fransson, J.-E. Bäckvall, J. Org. Chem. 2006, 71, 8622-8625; k) N. J. Alcock, I. Mann, P. Peach, M. Wills, Tetrahedron: Asymmetry 2002, 13, 2485-2490; 1) I. C. Lennon, J. A. Ramsden, Org. Process Res. Dev. 2005, 9, 110-112; m) T. Kioke, K. Murata, T. Ikariya, Org. Lett. 2000, 2, 3833-3836.

[6] For relevant reviews see: a) J. Barrios-Rivera, Y. Xu, M. Wills, Org. Biomol. Chem. 2019, 7, 1301-1321; b) F. Foubelo, C. Nájera, M. Yu, Tetrahedron: Asymmetry 2015, 26, 769-790; c) A. Zoabi, S. Omar, R. Abu-Reziq, Eur. J. Org. Chem., 2015, 2101-2109; d) J. G. Deng, Y. Q. Tu, S. H. Wang, Chem. Commun. 2004, 2070-2071; e) P. N. Liu, P. M. Gu, J. G. Deng, Y. Q. Tu, Y. P. Ma, Eur. J Org. Chem. 2005, 3221-3227; f) R. N. Liu, P. M. Gu, F. Wang, Y. Q. Tu, Org. Lett. 2004, 6, 169-172; g) R. Liu, T. Cheng, L. Kong, C. Chen, G. Liu, H. Li, J. Catal. 2013, 307, 55-61; h) J. Li, Y. Zhang, D. Han, Q. Gao, C. Li, J. Mol. Cat. A: Chemical 2009, 298, 31-35; i) X. Huang, J. Y. Ying, Chem. Commun. 2007, 1825-1827; j) D. Zhang, J. Xu, Q. Zhao, T. Cheng, G. Liu, ChemCatChem 2014, 6, 2998-3003.

[7] a) R. Wang, J. Wan, X. a, X. Xu, L. Liu, J. Chem Soc. Dalton Trans. 2013, 42, 6513-6522; b) X. Xu, R. Wang, J. Wan, X. Ma, J. Peng, RSC Adv. 2013, 3, 6747-6751; c) N. Haraguchi, K. Tsuru, Y. Arakawa, S. Itsuno, Org. Biomol. Chem. 2009, 7, 69-75; d) R. Marcos, C. Jimeno, M. A. Percias, Adv. Synth. Catal. 2011, 353, 1345-1352; e) R. Akiyama, S. Kobayashi, Angew Chem. Int Ed. 2002, 41, 2602-2604; f) Y. Arakawa, A. Chiba, N. Haraguchi, S. Itsuno, Adv. Synth Catal. 2008, 350, 2295-2304; g) C. M. Zammit, M. Wills, Tetrahedron: Asymmetry 2013, 24, 844-852.

[8] a) W. Shan, F. Meng, Y. Wu, F. Mao, X. Li. J. Organomet. Chem. 2011, 696, 1687 1690; b) J. Liu, Y. Zhou, Y. Wu, X. Li, A. S. C. Chan, Tetrahedron: Asymmetry 2008, 19, 832-837; c) H. F. Zhou, Q. H. Fan, Y. Y. Huang, L. Wu, Y. M. He, W. J. Tang, L. Q. Gu, A. S. C. Chan, J. Mol. Cat. A: Chemical 2007, 275, 47-53; d) Y. Wu, C. Lu, W. Shan, X. Li, Tetrahedron: Asymmetry 2009, 20, 584-587.

[9] a) X. Li, X. Wu, W. Chen, F. E. Hancock, F. King. J. Xiao, Org. Lett. 2004, 6, 3321-3324; b) X. Li, W. Hems, F. King, J. Xiao, Tetrahedron Lett. 2004, 45, 951-953.

[10] J. M. Zimbron, M. Dauphinais, A. B. Charette, Green Chem. 2015, 17, 3255-3259.

[11] a) I. Kawasaki, K. Tsunoda, T. Tsuji, T. Yamaguchi, H. Shibuta, N. Uchida, M. Yamashita, S. Ohta, Chem. Commun. 2005, 2134-2135; b) T. J. Geldbach, P. J. Dyson, J. Am. Chem. Soc. 2004, 126, 8114-8115.

[12] a) Y. C. Chen, T. F. Wu, L. Jiang, J. G. Deng, H. Liu, J. Zhu, Y. Z. Jiang, J. Org. Chem. 2005, 70, 1006-1010; b) W. Liu, X. Cui, L. Cun, J. Zhu, J. Deng, Tetrahedron: Asymmetry 2005, 16, 2525-2530.

[13] a) Y. Zhao, R. Jin, Y. Chan, Y. Li, J. Lin, G. Liu, RSC Adv. 2017, 7, 22592-22598; b) G. Zhang, T. Liu, Y. Chou, Y. Wang, T. Cheng, G. Liu, ChemCatChem 2018, 10, 1882-1888; c) M. Gao, F. Chang, S. Wang, Z. Liu, Z. Zhao, G. Liu, J. Catal. 2019, 370, 191-197; d) J. Meng, F. Chang, Y. Su, R. Liu, T. Cheng, G. Liu, ACS Catal. 2019, 9, 8693-8701.

[14] S. B. Wendicke, E. Burris, R. Scopelliti, K. Severin, Organometallics 2003, 22, 1894-1897.

[15] T. Cheng, Q. Zhao, D. Zhang, G. Liu, Green Chem. 2015, 17, 2100-2122.

[16] S. H. Yang, S. Chang, Org. Lett. 2001, 3, 2089-2091.

[17] Y. Na, S. Chang, Org. Lett. 2000, 2, 1887-1889. P. J. Dyson, D. J. Ellis, T. Welton, J. Am. Chem. Soc. 2002, 124, 9334-9335.

[19] a) U. Karlsson, G.-Z. Wang, J.-E. Backvall, J. Org. Chem. 1994, 59, 1196-1198; b) M. Lee, S. Chang, Tetrahedron Lett. 2000, 41, 7507-7510.

[20] a) D. L. Davies, J. Fawcett, S. A. Garratt, D. R. Russell, Organometallics 2001, 20, 3029-3034; b) J. W. Faller, B. J. Grimmond, Organometallics 2001, 20, 2454-2458; c) D. L. Davies, J. Fawcett, S. A. Garratt, D. A. Russell, Chem. Commun. 1997, 1352-1352.

[21] a) F. Simal, A. Demonceau, A. F. Noels, Tetrahedron Lett. 1998, 39, 3493-3496. (b) F. Simal, D. Jan, A. Demonceau, A. F. Noels, Tetrahedron Lett. 1999, 40, 1653-1656.

[22] S. Doherty, C. R. Newman, R. K. Rath, M. Nieuwenhuyzen, J. G. Knight, W. Clegg Organometallics 2005, 24, 2633-2644.

[23] For ring closing metathesis see: a) E. L. Dias, R. H. Grubbs, Organometallics 1998, 17, 2758-2767; b) A. Fürstner, M. Picquet, C. Bruneau, P. H. Dixneuf, Chem. Commun. 1998, 1315-1316; c) A. Fürstner, M. Liebl, C. W. Lehmann, M. Picquet, R. Kunz, C. Bruneau, D. Touchard, P. H. Dixneuf, Chem. Eur. J. 2000, 6, 1847-1857; d) A. Furstner, L. Ackermann, Chem. Commun. 1999, 95-96. For ring-opening metathesis see: e) A. Hafner, A. Mühlebach, P. A. van der Schaaf, Angew. Chem. Int. Ed. Engl. 1997, 36, 2121-2124; f) A. Demonceau, A. W. Stumpf, E. Saive, A. F. Noels, Macromolecules 1997, 30, 3127-3136; g) A. W. Stumpf, E. Saive, A. Demonceau, A. F. Noels, J. Chem. Soc., Chem. Commun. 1995, 1127 1128.

[24] a) T. Touge, T. Hakamata, H. Nara, T. Kobayashi, N. Sayo, T. Saito, Y. Kayaki, T. Ikariya, J. Am. Chem. Soc. 2011, 133, 14960-14963; b) P. Mörschel, J. Janikowski, G. Hilt, G. Frenking, J. Am. Chem Soc. 2008, 130, 8952-8966.

[25] T. Meng, Q.-P. Qin, Z.-L. Chen, H.-H. Zou, K. Wang, F.-P. Liang, Dalton Trans. 2019, 48, 5352-5360.

[26] J. Soleimannejad, C. White, Organometallics 2005, 24, 2538-2541.

[27] B. Therrien, G. Suss-Fink, Inorg. Chim. Acta 2006, 359, 4350-4354.

[28] F. Martínez-Pena, S. Infante-Tadeo, A. Habtemariam, A. M. Pizarro, Inorg. Chem. 2018, 57, 5657-5668.

[29] a) K.-J. Haack, S. Hashiguchi, A. Fujii, T. Ikariya, R. Noyori, Angew Chem. Int. Ed. 1997, 36, 285-288; b) N. Uematsu, A. Fujii, S. Hashiguchi, T. Ikariya, R. Noyori, J. Am. Chem. Soc. 1996, 118, 4916-4917.

[30] B. Vilhanová, J. Václavík, P. Šot, J. Pecháček, J. Zápal, R. Pažout, J. Maixner, M. Kuzma, P. Kačer, Chem Commun. 2016, 52, 362-365.

[31] J. Soleimannejad, A. Sisson, C. White, Inorg. Chim. Acta 2003, 352, 121-128.

[32] a) S. Bai, H. Yang, P. Wang, J. Gao, B. Li, Q. Yang, C. Li, Chem. Commun. 2010, 46, 8145-8147; b) H. Yang, J. Li, J. Yang, Z. Liu, Q. Yang, C. Li, Chem. Commun. 2007, 1086-1088.

[33] a) J. M. Thomas, T. Maschmeyer, B. F. G. Johnson, D. S. Shepard, J. Mol. Cat. A: Chem. 1999, 141, 139-144; b) F. Goettmanna, C. Sanchez, J. Mater. Chem. 2007, 17, 24-30; c) V. Mouarrawis, R. Plessius, J. I. van der Vlugt, J. N. H. Reek, Frontiers in Chem. 2018, 6, 623.

[34] B. Pugin, J. Mol. Cat. A: Chem. 1996, 107, 273-279.

[35] a) M. Yamakawa, I. Yamada, R. Noyori, Angew. Chem. Int. Ed. 2001, 40, 2818-2821; b) D. J. Morris, A. M. Hayes, M. Wills, J. Org. Chem. 2006, 71, 7035-7044. 10.1002/ejic.202000948 Accepted Manuscript European Journal of Inorganic Chemistry

[36] A. M. R. Hall, P. Dong, A. Codina, J. P. Lowe, U. Hintermair, ACS Catal. 2019, 9, 2079-2090.

[37] L. Vieille-Petit, B. Therrien, G. Süss-Fink, Eur. J. Inorg. Chem. 2003, 20, 3707-3711.

[38] R. C. Clark, J. S. Reid, Acta Cryst. 1995, A51, 887-897.

[39] CrysAlisPro, Rigaku Oxford Diffraction, Tokyo, Japan.

[40] G. M. Sheldrick, Acta Cryst. 2015, A71, 3-8.

[41] G. M. Sheldrick, Acta Cryst. 2008, A64, 112-122.
[42] O. V. Dolomanov, L. J. Bourhis, R. J. Gildea, J. A. K. Howard, H. Puschmann, J. Appl. Cryst. 2009, 42, 339-341.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

ACKNOWLEDGMENT

The authors extend their appreciation to the Deputyship for Research & Innovation, Ministry of Education in Saudi Arabia for funding this research work through the project number (2021-044) and King Abdulaziz University, DSR, Jeddah, Saudi Arabia.

We claim:

1. A method of catalyzing asymmetric hydrogenation of a ketone, comprising
    contacting the ketone with a hydrogen donor in the presence of the arene-Ru (II) catalyst having the formula

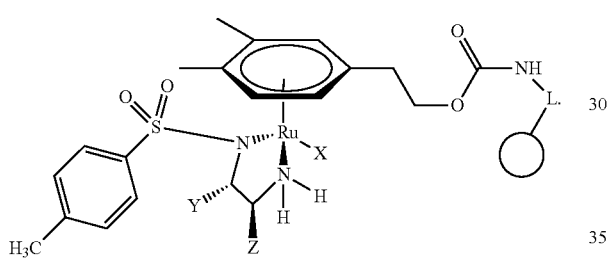

wherein X is a halogen or CN,
Y and Z are the same or different and each is a carbon ring structure;
L is a carbon linker; and
◯ is a silica support.

2. The method of claim 1, wherein the ketone is:

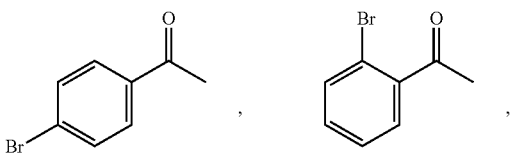

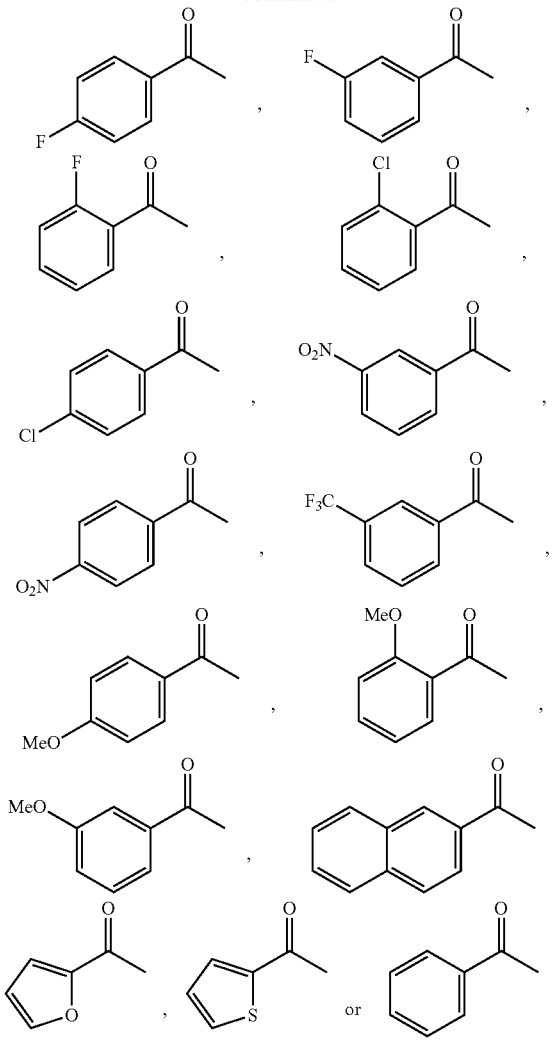

3. The method of claim 1, wherein the hydrogen donor is $HCO_2H/NEt_3$, $Me_2NHBH_3$, $NaBH_4$, $KO_2CH$, $NH_4O_2CH$ or $HCO_2H$.

4. The method of claim 1, wherein the method is conducted by or incorporated into a continuous flow process.

5. The method of claim 1, wherein the arene-Ru (II) catalyst is generated in situ.

* * * * *